US012127787B2

(12) United States Patent
Butterworth et al.

(10) Patent No.: US 12,127,787 B2
(45) Date of Patent: Oct. 29, 2024

(54) NON-INVASIVE SKIN CONTACT SENSOR

(71) Applicant: Massachusetts Institute of Technology, Cambridge, MA (US)

(72) Inventors: Ian R. Butterworth, Cambridge, MA (US); Luca Daniel, Cambridge, MA (US); Jose E. Cruz Serralles, Cambridge, MA (US); William Peter Hansen, Canaan, NY (US); Petra B. Krauledat, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 859 days.

(21) Appl. No.: 16/729,923

(22) Filed: Dec. 30, 2019

(65) Prior Publication Data
US 2020/0205895 A1 Jul. 2, 2020

Related U.S. Application Data

(60) Provisional application No. 62/786,652, filed on Dec. 31, 2018.

(51) Int. Cl.
*A61B 18/18* (2006.01)
*A61B 5/00* (2006.01)
(Continued)

(52) U.S. Cl.
CPC ........ *A61B 18/1815* (2013.01); *A61B 5/0053* (2013.01); *A61B 5/01* (2013.01);
(Continued)

(58) Field of Classification Search
CPC ... A61B 5/6843; A61B 5/4878; A61B 5/4869; A61B 5/0048; A61B 5/6833;
(Continued)

(56) References Cited

U.S. PATENT DOCUMENTS 3,818,333 A 6/1974 Walker
3,851,244 A 11/1974 Mounce
(Continued)

FOREIGN PATENT DOCUMENTS

EP 1 248 561 B1 6/2006
EP 2 465 428 A1 6/2012
(Continued)

OTHER PUBLICATIONS

PCT International Preliminary Report on Patentability dated Jul. 15, 2021 for International Application No. PCT/US2019/068886; 11 Pages.

(Continued)

*Primary Examiner* — Eric J Messersmith
*Assistant Examiner* — Chanel J Jhin
(74) *Attorney, Agent, or Firm* — DALY, CROWLEY, MOFFORD & DURKEE, LLP

(57) ABSTRACT

A system and method for measuring a hydration level in human tissue. The system includes a coaxial probe have a first end configured to be in contract with human tissue and configured to be emit and receive signals associated with a spectroscopic technique and having a second end adapted to be coupled to transmit and receive circuitry. The system further includes a patch or other means coupled to the coaxial probe and configured to be adhered to human tissue so as to provide a force upon at least a portion of the coaxial probe configured to be in contact with human tissue. In embodiments, the system may further include means coupled to receive signals from the coaxial probe, for determining an amount of liquid within a portion of human tissue in contact with the first end of the probe.

8 Claims, 13 Drawing Sheets

(51) Int. Cl.
    *A61B 5/01*           (2006.01)
    *A61B 5/0537*       (2021.01)
    *A61B 18/00*        (2006.01)
    *A61B 18/22*        (2006.01)
(52) U.S. Cl.
    CPC ............ *A61B 5/0537* (2013.01); *A61B 5/443* (2013.01); *A61B 5/4875* (2013.01); *A61B 5/6833* (2013.01); *A61B 2018/00791* (2013.01); *A61B 2018/00964* (2013.01); *A61B 2018/2233* (2013.01)
(58) Field of Classification Search
    CPC ..... A61B 5/4875; A61B 5/443; A61B 5/0537; A61B 5/01; A61B 5/0053; A61B 2018/2233; A61B 2018/00964; A61B 2018/00791; A61B 18/1815
    See application file for complete search history.

(56) References Cited

U.S. PATENT DOCUMENTS

| | | | |
|---|---|---|---|
| 4,319,185 | A | 3/1982 | Hill |
| 4,620,146 | A | 10/1986 | Ishikawa et al. |
| 4,674,325 | A | 6/1987 | Kiyobe et al. |
| 4,812,739 | A | 3/1989 | Swanson |
| 6,057,761 | A | 5/2000 | Yukl |
| 6,370,426 | B1 | 4/2002 | Campbell et al. |
| 2003/0072549 | A1* | 4/2003 | Facer ............... G01N 22/00 385/12 |
| 2004/0012398 | A1 | 1/2004 | Bailey et al. |
| 2005/0070778 | A1* | 3/2005 | Lackey ............ A61B 5/4875 600/366 |
| 2005/0177061 | A1 | 8/2005 | Alanen et al. |
| 2005/0267342 | A1* | 12/2005 | Blank .............. G01N 21/359 600/316 |
| 2007/0159592 | A1* | 7/2007 | Rylander ......... A61B 5/0075 351/44 |
| 2008/0221408 | A1 | 9/2008 | Hoarau et al. |
| 2010/0081960 | A1 | 4/2010 | McKenna |
| 2013/0289365 | A1* | 10/2013 | Vain ................. A61B 5/103 600/301 |
| 2018/0020948 | A1 | 1/2018 | Butterworth et al. |
| 2018/0042513 | A1* | 2/2018 | Connor ............ A61B 5/6824 |
| 2018/0231475 | A1 | 8/2018 | Brown et al. |

FOREIGN PATENT DOCUMENTS

| | | |
|---|---|---|
| GB | 1 593 173 4 | 7/1981 |
| WO | WO 02/14848 A1 | 2/2002 |
| WO | WO 03/009753 A2 | 2/2003 |
| WO | WO 2018/156624 | 8/2018 |

OTHER PUBLICATIONS

International Search Report and Written Opinion of the ISA dated Mar. 25, 2020 for International Application No. PCT/US2019/068886; 19 Pages.
Agilent Technologies; "Agilent Basics of Measuring the Dielectric Properties of Materials"; Jun. 26, 2006; 32 Pages.
Agilent Technologies; "Measure the Difference"; Microwave Dielectric Spectroscopy Workshop; Jan. 2004; 42 Pages.
Albert; "Fluid Management Strategies in Heart Failure"; Critical Care Nurse; vol. 32; No. 2; Apr. 2012; 15 Pages.
Albert, et al; "Vasopressin Response to Dehydration in Alzheimer's Disease"; American Geriatrics Society; vol. 37; No. 9; Sep. 1989; 5 Pages.
Anand, et al.; "Monitoring Changes in Fluid Status With a Wireless Multisensor Monitor: Results From the Fluid Removal During Adherent Renal Monitoring (FARM) Study"; Congest Heart Fail; vol. 18; No. 1; Jan./Feb. 2012; 5 Pages.

Ancukiewics, et al.; "Standardized Method for Quantification of Developing Lymphedema in Patients Treated for Breast Cancer"; Int. J. Radiation Oncology Biol. Phys.; vol. 79; No. 5; pp. 1436-1443; Jan. 2011; 8 Pages.
Arimoto, et al.; "Depth profile of diffuse reflectance near-infrared spectroscopy for measurement of water content in skin"; Skin Research and Technology; pp. 27-35; Jan. 2005; 9 Pages.
Armstrong; "Assessing Hydration Status: The Elusive Gold Standard"; Journal of the American College of Nutrition; vol. 26; No. 5; pp. 575S-584S; Jul. 16, 2007; 10 Pages.
Armstrong; "Challenges of linking chronic dehydration and fluid consumption to health outcomes"; Nutrition Reviews; vol. 70(Suppl. 2); pp. S121-S127; Jan. 2012; 7 Pages.
Armstrong; "Hydration Assessment Techniques"; Nutrition Reviews; vol. 63; No. 6; pp. S40-S54; Jun. 2005; 16 Pages.
Barthel, et al.; "Dielectric Spectra Of Some Common Solvents In The Microwave Region. Dipolar Aprotic Solvents And Amides"; Chemical Physics Letters; vol. 167; No. 1,2; Mar. 16, 1990; 5 Pages.
Beck; "Defending a delicate balance of fluid and electrolytes"; The Aging kidney; Nephrology; Geriatrics; vol. 55; No. 4; Apr. 2000; 5 Pages.
Beckmann, et al.; "Portable Bioimpedance Spectroscopy device and textile electrodes for mobile monitoring applications"; International Conference on Electrical Bioimpedance; Journal of Physics: Conference Series 224; Jan. 2010; 4 Pages.
Beckmann, et al.; "Monitoring change of body fluids during physical exercise using Bioimpedance Spectroscopy"; 31st Annual International Conference of the IEEE EMBS; Sep. 2-6, 2009; 4 Pages.
Begum; "A review of the literature on dehydration in the institutionalized elderly"; e-SPEN, the European e-Journal of Clinical Nutrition and Metabolism 5; pp. e47-e53; Oct. 23, 2009; 7 Pages.
Bennett, et al.; "Unrecognized Chronic Dehydration in Older Adults; Examining Prevalence Rate and Risk Factors"; Journal of Gerontological Nursing; pp. 22-28; Nov. 2004; 8 Pages.
Blaxter, et al.; "An Automated quasi-continuous capillary refill timing device"; IOP Publishing; Institute od Physics and Engineering in Medicine; Physiological Measurement 37; pp. 83-99; Dec. 7, 2015; 18 Pages.
Brachmann, et al.; Fluid status monitoring with a wireless network to reduce cardiovascular-related hospitalizations and mortality in heart failure: rationale and design of the OptiLink HF study (Optimization of Heart Failure Management using OptiVol Fluid Status Monitoring and CareLink); European Journal of Heart Failure 13; pp. 796-804; May 8, 2011; 10 Pages.
Bruera, et al.; "Effects of Parenteral Hydration in Terminally Ill Cancer Patients: A Preliminary Study"; Journal of Clinical Oncology; vol. 23; No. 10; pp. 2366-2371; Apr. 1, 2005; 7 Pages.
Bryant; "Dehydration in Older People: Assessment and Management"; emergency nurse; vol. 15; No. 4; pp. 22-26; Jul. 2007; 6 Pages.
Bunn, et al.; Effectiveness of external factors to reduce dehydration risk in older people living in residential care: a systematic review; National Institute for Health Research; Date Unknow; 1 Page.
Campbell; "Cornwall Hydration Project"; Peninsula Community Health; Jan. 2014; 28 Pages.
Campbell; Innovations to support hydration care across health and social care; 2016 MA Healthcare Ltd; Nutrition; pp. S24-S29; Jun./Jul. 2016; 7 Pages.
Campbell; "Recognising and preventing dehydration among patients"; Nursing Practice; Hydration; Nursing Times 12.11.14; vol. 110; No. 46; pp. 20-21; 2 Pages.
Catanzariti, et al.; "Monitoring Intrathoracic Impedance with an Implantable Defibrillator Reduces Hospitalizations in Patients with Heart Failure"; PACE; vol. 32; pp. 363-370; Mar. 2009; 9 Pages.
Chamberlain; "Looking at Biological Syste S With Terahertz Radiation"; Durham University; NPL Terahertz Workshop; Dec. 17, 2009; 56 Pages.
Cheuvront, et al.; "Biological variation and diagnostic accuracy of dehydration assessment markers[1–4]"; The American Journal of Clinical Nutrition; pp. 565-573; Jan. 2010; 9 Pages.

(56) References Cited

OTHER PUBLICATIONS

Cheuvront, et al; "Comparison between blood and urinary indices for dehydration: a different interpretation"; Springer-Verlag Berlin Heidelberg; Eur J Appl Physiol 113; pp. 2167-2168; May 28, 2013; 2 Pages.
Cheuvront, et al; "Physiological basis for understanding quantitative dehydration assessment[1-4]"; The American Journal of Clinical Nutrition; pp. 455-462; Jan. 2013; 8 Pages.
Cheuvront, et al; "Reference change values for monitoring dehydration"; Clin Chem Lab Med; Jan. 2011; 5 Pages.
Cheuvront; "Urinalysis for hydration assessment: an age-old problem[1]"; The American Journal of Clinical Nutrition; pp. 3-4; Jun. 2016; 2 Pages.
Clark, et al.; "Causes and treatment of oedema in patients with heart failure"; Nature Reviews; Cardiology; vol. 10; pp. 156-170; Mar. 2013; 15 Pages.
Constantin, et al.; "Skin Hydration Assessment through Modern Non-Invasive Bioengineering Technologies"; Medica—a Journal of Clinical Medicine; pp. 33-38; Feb. 13, 2014; 6 Pages.
Covic, et al.; "Time to Improve Fluid Management in Hemodialysis: Should We Abandon Clinical Assessment and Routinely Use Bioimpedance?"; American Society of Nephrology; vol. 8; pp. 1474-1475; Sep. 2013; 2 Pages.
D'Anci, et al.; "Hydration and Cognitive Function in Children"; Nutrition in Clinical Care; Nutrition Reviews, vol. 64; No. 10; pp. 457-464; Oct. 2006; 9 Pages.
Danylov; "THz Laboratory Measurements of Atmospheric Absorption Between 6% and 52% Relative Humidity"; Submillimeter-Wave Technology Laboratory; Sep. 2006; 7 Pages.
Daugirdas; "Bioimpedance Technology and Optimal Fluid Management"; AJKD; pp. 861-864; Jan. 2013; 4 Pages.
Davenport, et al; "Fluids, Electrolytes, and Dehydration"; Handbook of Pediatric Surgery; 2.1 Fluids, Electrolytes and Dehydration; pp. 9-19; Jan. 2010; 12 Pages.
Deng, et al.; "In Vitro Measurements of Inertial Cavitation Thresholds in Human Blood"; Ultrasound in Med & Biol., vol. 22; No. 7; pp. 939-948; Apr. 4, 1996; 10 Pages.
Di Somma, et al.; "The emerging role of Biomarkers and bioimpedance in evaluating hydration status in patients with acute heart failure"; Clin Chem Lab Med; pp. 2093-2105; Sep. 19, 2012; 13 Pages.
Dimitrieva, et al.; "Increased Insensible Water Loss Contributes to Aging Related Dehydration"; Increased Insensible Water Loss; PLOS One; vol. 6; Issue 5; May 2011; 5 Pages.
Ellis, et al.; "Human hydrometry: comparison of multifrequency bioelectrical impedance with $^2H_2O$ and bromine dilution"; Body Water Measurements; The American Physiological Society; pp. 1056-1062; Jan. 1998; 7 Pages.
El-Sharkawy, et al.; "Hydration and outcome in older patients admitted to hospital (The HOOP prospective cohort study)"; Age and Ageing Advance; Aug. 26, 2015; 6 Pages.
Ely, et al; "Assessment of extracellular dehydration using saliva osmolality"; Eur J Appl Physiol; pp. 85-92; Oct. 23, 2013; 8 Pages.
Evans, et al.; "Factors Affecting the In Vivo Precision of Bioelectrical Impedance Analysis"; Appl. Radiat. Isot., vol. 49; No. 5/6; pp. 485-487; Jan. 1998; 4 Pages.
Feinsod, et al.; "Dehydration in Frail, Older Residents in Long-Term Care Facilities"; JAMDA; Mar./Apr. 2004; 6 Pages.
Ferry; "Strategies for Ensuring Good Hydration in the Elderly"; Nutrition Reviews, vol. 63; No. 6; pp. S22-S29; Jun. 2005; 8 Pages.
Fleming, et al.; "The Diagnostic Value of Capillary Refill Time for Detecting Serious Illness in Children; A systematic Review and Meta-Analysis"; Diagnostic Value of Capillary Refill Time in Children; PLOS ONE; Sep. 16, 2015; 16 Pages.
Fortes, et al.; Is This Elderly Patient Dehydrated? Diagnostic Accuracy of Hydration Assessment Using Physical Signs, Urine, and Saliva Markers; JAMDA 16; pp. 221-228; Jan. 2015; 8 Pages.
Frangeskou, et al.; "Dehydration in the Elderly: A Review Focused on Economic Burden"; J Nutr Health Aging; vol. 19; No. 6; pp. 619-627; Jul. 3, 2014; 9 Pages.

Fruhstorfer, et al.; "Thickness of the Stratum Corneum of the Volar Fingertips"; Clinical Anatomy 13; pp. 429-433; Jan. 2000; 5 Pages.
Gallagher; "The Hight Cost of Poor Care: The Financial Case for Prevention in American Nursing Homes"; The National Consumer Voice for Quality Long-Term Care; Apr. 2011; 9 Pages.
Gorelick, et al.; "Validity and Reliability of Clinical Signs in the Diagnosis of Dehydration in Children"; Pediatrics; vol. 99; No. 5; May 1997; 8 Pages.
Gross, et al.; "Clinical Indicators of Dehydration Severity in Elderly Patients"; The Journal of Emergency Medicine; vol. 10; pp. 267-274; Oct. 30, 1991; 8 Pages.
Gudivaka, et al.; Effect of Body Position, Electrode Placement and Time on Prediction of Total Body Water by Multifrequency Bioelectrical Impedance Analysis; Age & Nutrition; vol. 5; No. 2; pp. 111-117; Jan. 1994; 7 Pages.
Hirsch, et al.; "Nanoshell-mediated near-infrared thermal therapy of tumors under magnetic resonance guidance"; PNAS; vol. 100; No. 23; pp. 13549-13554; Nov. 11, 2003; 6 Pages.
Ho, et al.; "Bioimpedance analysis of total body water in hemodialysis patients"; Kidney International; vol. 46; pp. 1438-1442; Jun. 23, 1994; 5 Pages.
Ho, et al.; "Wireless power transfer to deep-tissue microimplants"; PNAS; vol. 111; No. 22; pp. 7974-7979; Jun. 3, 2014; 6 Pages.
Hooper, et al.; "Water-loss (intracellular) dehydration assessed using urinary tests: how well do they work? Diagnostic accuracy in older people[1-3]"; American Society for Nutrition; Jan. 2016; 11 Pages.
Hooper, et al.; "Water-loss dehydration and aging"; Mechanisms of Aging and Development 136-137; pp. 50-58; Jan. 2014; 9 Pages.
Horn, et al.; "Quantifying Dehydration in the Fire Service Using Field Methods And Novel Devices"; Prehospital Emergency Care; vol. 16; No. 3; pp. 347-355; Jul./Sep. 2012; 9 Pages.
Hoxha, et al.; "Performance of Clinical Signs in the Diagnosis of Dehydration in Children with Acute Gastroenteritis"; Med Arh.; pp. 10-12; Feb. 2015; 3 Pages.
Hur, et al.; "Effect of Fluid Management Guided by Bioimpedance Spectroscopy on Cardiovascular Parameters in Hemodialysis Patients: A Randomized Controlled Trial"; AJKD; pp. 957-965; Jan. 2013; 9 pages.
Jonas; "Novel Modality for Fluid Monitoring"; Kyma Medical Technologies; Date Unknown; 17 Pages.
Lloyd-Jones, et al.; "Heart Disease and Stroke Statistics—2010 Update: A Report From the American Heart Association"; Dec. 17, 2009; 173 Pages.
Kaatze, et al.; "Dielectric Properties of Organic Solute/Water Mixtures. Hydrophobic Hydration and Relaxation"; Journal of Molecular Liquids, vol. 52; pp. 181-210; Jan. 1992; 30 Pages.
Khalil, et al.; "The Theory and Fundamentals of Bioimpedance Analysis in Clinical Status Monitoring and Diagnosis of Diseases"; Sensors; Jun. 19, 2014; 34 Pages.
Kikawa, et al.; "A Presence-detection Method using RRSI of a Bluetooth Device"; International Journal of Informatics Society; vol. 2; No. 1; pp. 23-31; Jan. 2010; 9 Pages.
Kviesis-Kipge, et al.; "Real-time analysis of skin capillary-refill processes using blue LED"; Proc. Of SPIE; vol. 7115, 771523; Jan. 2010; 7 Pages.
Kirkland, et al.; "Patterns of urine flow and electrolyte excretion in healthy elderly people"; British Medical Journal; vol. 287; pp. 1665-1667; Dec. 3, 1983; 3 Pages.
Kushner, et al.; "Clinical characteristics influencing bioelectrical impedance analysis measurements[1-3]"; American Journal of Clinical Nutrition; pp. 423S-427S; Jan. 1996; 6 pages.
Kushner, et al.; "Estimation of total body water by bioelectrical impedance analysis"; American Journal of Clinical Nutrition 44; pp. 417-424. Sep. 1986; 9 Pages.
Leaf; "Dehydration in the Elderly"; The New England Journal of Medicine; vol. 311; No. 12; pp. 791-792; Sep. 20, 1984; 2 Pages.
Lecko; "Patient Safety and nutrition and hydration in the elderly"; The Health Foundation Inspiring Improvement; May 2013; 7 Pages.
Le Pennec, et al.; "2.4 GHz Radio Transmission Measurements in a Basin filled with Sea Water"; Date Unknown; 4 Pages.

(56) References Cited

OTHER PUBLICATIONS

Li, et al.; "Flanged Coaxial Microwave Probes for Measuring Thin Moisture Layers"; IEEE Transactions on Biomedical Engineering; vol. 39; No. 1; pp. 49-57; Jan. 1992; 9 Pages.

Lindeman, et al.; "Do Elderly persons Need to Be Encouraged to Drink More Fluids?"; The Gerontological Society of America; Journal of Gerontology: Medical Sciences; vol. 55A; No. 7; pp. M361-M365; Jan. 2000; 5 Pages.

Mange, et al.; "Language Guiding Therapy: The Case of Dehydration versus vol. Depletion"; Annals of Internal Medicine; vol. 127; No. 9; pp. 848-853; Nov. 1, 1997; 6 Pages.

Manzone, et al.; "Blood Volume Analysis: A New Technique and New Clinical Interest Reinvigorate a Classic Study"; Journal of Nuclear Medicine Technology; vol. 35; No. 2; pp. 55-63; Jun. 2007; 9 Pages.

Bourdel-Marchasson, et al.; "One-Year Incidence of Hyperosmolar States and Prognosis in a Geriatric Acute Care Unit"; Gerontology; pp. 171-176; May 28, 2003; 7 Pages.

Marquez, et al.; "Skin-Electrode Contact Area in Electrical Bioimpedance Spectroscopy. Influence in Total Body Composition Assessment"; 33rd Annual International Conference of the IEEE Embs; pp. 1867-1870; August 30-Sep. 3, 2011; 4 Pages.

Maughan; "Impact of mild dehydration on wellness and on exercise performance"; European Journal of Clinical Nutrition; vol. 57; Suppl 2; pp. S19-S23; Jan. 2003; 5 Pages.

McDonald; "Monitoring Fluid Status at the Outpatient Level: The Need for More Precision"; Supplement 1; Jul./Aug. 2010; 5 Pages.

Medtronic; "Clinicians Practical Guide for Using OptiVol® and other Trends for Managing Heart Failure Patients"; Apr. 2008; 33 Pages.

Moller, et al.; "Epidermal Thickness at Different Body Sites: Relationship to Age, Gender, Pigmentation, Blood Content, Skin Type and Smoking Habits"; Acta Derm Venereol; pp. 410-413; Jan. 2003; 4 Pages.

Moran, et al.; "Hydration status measurement by radio frequency absorptiometry in young athletes—a new method and preliminary results"; Institute of Physics Publishing; Physiol. Meas. 25; pp. 51-59; Jan. 2004; 10 Pages.

Moran, et al.; "Hypohydration Measurements by Radio Frequency"; RTO-MP-HFM-086; Dec. 2003; 8 Pages.

Moreno, et al.; "Evaluation of a new impedancemeter to independently measure extracellular, intracellular and total body water volumes: application to the measurement of hydration"; Med Biol Eng Comput; Jun. 3, 2015; 11 Pages.

Morris, et al.; "Cognitive Performance Scale"; Journal of Gerontology: Medical Sciences 49 (4); Jan. 1994; 1 Page.

Lavizzo-Mourey, et al.; "Risk Factors for Dehydration Among Elderly Nursing Home Residents"; American Geriatrics Society; JAGS—vol. 36; No. 3; pp. 213-218; Mar. 1988; 6 Pages.

Vinh; "Probing the dynamics of biomolecules in liquid water by terahertz spectroscopy"; Institute of Terahertz Science and Technology; Sep. 2010; 25 Pages.

NHS England; "Guidance—Commissioning Excellent Nutrition and Hydration"; Jan. 2015-Jan. 2018; 29 Pages.

National Institute for Health and Care Excellence; "Acute kidney injury—Prevention, detection and management of acute kidney injury up to the point of renal replacement therapy"; NICE clinical guidelines 169; Aug. 2013; 39 Pages.

NIH; "What Causes Hypotension"; National Heart, Lung, and Blood Institute; Jun. 28, 2017; 13 Pages.

Ouslander, et al.; "Potentially Avoidable Hospitalizations of Nursing Home Residents: Frequency, Causes, and Costs"; The American Geriatrics Society; vol. 58; No. 4; pp. 627-635; Apr. 2010; 9 Pages.

Peacock, et al.; "Current Technique of Fluid Status Assessment"; CME; pp. S45-S51; Jul./Aug. 2010; 7 Pages.

Phillips; "Disturbed Fluid and Electrolyte Homoeostasis Following Dehydration in Elderly People"; Age and Ageing; pp. S27-S33; Jan. 1993; 8 Pages.

Phillips, et al.; "Reduced Oropharyngeal Inhibition of AVP Secretion in Dehydrated Elderly Mena"; Annals New York Academy of Sciences; pp. 651-655; Date Unknown; 6 Pages.

Phillips, et al.; "Reduced Thirst After Water Deprivation in Healthy Elderly Men"; The New England Journal of Medicine; pp. 753-759; Sep. 20, 1984; 7 Pages.

Pollonini, et al.; "A Novel Handheld Device for Use in Remote Patient Monitoring of Heart Failure Patients—Design and Preliminary Validation on Healthy Subjects"; J Med Syst; pp. 653-659; Jan. 2012; 8 Pages.

Popkin, et al.; "Water, hydration, and health"; Nutrition Reviews; vol. 68(8); pp. 439-458; Jan. 2010; 21 Pages.

Popowski, et al.; "Blood and urinary measures of hydration status during progressive acute dehydration"; Official Journal of the American College of Sports Medicine; vol. 33; No. 5; pp. 747-753; Jan. 2001; 7 Pages.

Pruvost, et al.; "The Value of Body Weight Measurement to Assess Dehydration in Children"; PLOS ONE; vol. 8; Issue 1; Jan. 29, 2013; 6 Pages.

Rasouli, et al.; "Indicators of Dehydration and Hemoconcentration are Associated with the prevalence and Severity of Coronary Artery Disease"; Clinical and Experimental Pharmacology and Physiology; pp. 889-894; Jan. 2008; 7 Pages.

Robinson, et al.; "Dehydration Despite Drinking: Beyond the BUN/Creatinine Ratio"; JAMDA; pp.s S68-S71; Mar./Apr. 2004; 4 Pages.

Rodriguez, et al.; "The hydration influence on the risk of stroke (THIRST) study"; Neurocrit Care; pp. 187-194; Jan. 2009; 9 Pages.

Rolls, et al.; "Thirst following water deprivation in humans"; The American Physiological Society; Thirst in Humans; pp. R476-R482; May 1980; 7 Pages.

Romano, et al.; "MiSpec: A low-power microwave non-invasive sensor for detecting age-related, slow forming, dehydration"; Boston Biomedical Innovation Center; Date Unknown; 16 Pages.

Ramirez-Rubio, et al.; "Chronic Kidney disease in Nicaragua: a qualitative analysis of semi-structured interviews with physicians and pharmacists"; BioMed Central; Jan. 2013; 10 Pages.

Saavedra, et al.; "Capillary Refilling (Skin Turgor) in the Assessment of Dehydration"; AJDC; vol. 145; Capillary Refilling; pp. 296-298; Mar. 1991; 3 Pages.

Sabouni, et al.; "Study of Penetration Depth and Noise in Microwave Tomography Technique"; ACES Journal; vol. 28; No. 5; pp. 391-403; May 2013; 14 Pages.

Sarvazyan, et al.; "Ultrasonic assessment of tissue hydration status"; Ultrasonic 43; pp. 661-671; Mar. 26, 2005; 11 Pages Sawh; "Accuracy should be a priority for wearable technology tech according to survey Hydration and stress tracking on the wish list for the next gen wearables"; Jun. 27, 2016; 3 Pages.

Scharfetter, et al.; "Effect of postural changes on the reliability of vol. estimations from bioimpedance spectroscopy data"; Kidney International; vol. 51; pp. 1078-1087; Jan. 1997; 10 Pages.

Schlebusch, et al.; "On the road to a textile integrated bioimpedance early warning system for lung edema"; International Conference on Body Networks; Jan. 2010; 6 Pages.

Shavit, et al.; "A Novel Imaging Technique to Measure Capillary-Refill Time: Improving Diagnostic Accuracy for Dehydration in Young Children with Gastroenteritis"; Pediatrics; vol. 118; No. 6; pp. 2402-2408; Dec. 2006; 7 Pages.

Shibao, et al.; "Orthostatic Hypotension-Related Hospitalizations in the United States"; The American Journal of Medicine; vol. 120; No. 11; pp. 975-980; Nov. 2007; 6 Pages.

Shibata; Measurement of Complex Permittivity for Liquid Materials Using the Open-ended Cut-off Waveguide Reflection Method; CJMW; Jan. 2011; 4 Pages.

Silber, et al.; "Finger photoplethysmography during the Valsalva maneuver reflects left ventricular filling pressure"; American Physiological Society; pp. H2043-H2047; Mar. 2, 2012; 5 Pages.

Small; "Integrating Device-Based Monitoring into Clinical Practice: Insights from a Large Heart Failure Clinic"; The American Journal of Cardiology; vol. 99 (10A); May 21, 2007; 6 Pages.

Smith, et al.; "Use of Salivary Osmolality to Assess Dehydration"; Prehospital Emergency Care; vol. 16; No. 1; pp. 128-135; Jan./Mar. 2012; 9 Pages.

(56) References Cited

OTHER PUBLICATIONS

Spangler, et al; "The Management of Dehydration and Incontinence in Nonambulatory Geriatric Patients"; Journal of Applied Behavior Analysis; No. 3; pp. 397-401; Sep. 1984; 5 Pages.

Spigulis, et al.; "Contact probe pressure effects in skin multi-spectral photoplethysmography"; Proceedings of the SPIE—The International Society for Optical Engineering; Jun. 2007; 9 Pages.

Stinchcombe, et al.; "Seniors' Falls in Canada: Second Report: Key highlights"; Chronic Diseases and Injuries in Canada; vol. 34; No. 2-3; Jul. 2014; 4 Pages.

Stricker, et al.; "Hormones and Behavior: The Biology of Thirst and Sodium Appetite"; American Scientific; vol. 76; No. 3; pp. 261-267; May-Jun. 1988; 8 Pages.

Stromberg; "Patient-related factors of compliance in heart failure: some new insight into an old problem"; European Heart Journal; pp. 379-381; Jan. 2006; 4 Pages.

Tavassolian, et al.; A Novel Magnetic Relaxation-Based Platform for Hydration Monitoring; IEEE Sensors Journal; vol. 14; No. 8; Aug. 2014; 5 Pages.

Taylor, et al.; "THz Medical Imaging: in vivo Hydration Sensing"; IEEE Transactions on Terahertz Science and Technology; vol. 1; No. 1; pp. 201-219; Sep. 2011; 19 Pages.

Teruel-Briones; "Analysis of concordance between the bioelectrical impedance vector analysis and the bioelectrical impedance spectroscopy in haemodialysis patients"; Nefrologia; pp. 389-395; Jan. 2012; 7 Pages.

Thomas, et al.; "A Comparison of Segmental and Wrist-to-ankle Methodolgies of Bioimpedance Analysis"; Appl. Radiat. Isot.; vol. 49; No. 5/6; pp. 477-478; Jan. 1998; 4 Pages.

Thomas, et al.; "Bioimpedance Spectrometry in the Determination of Body Water Compartments: Accuracy and Clinical Significance"; Appl. Radiat. Isot.; vol. 49; No. 5/6; pp. 447-455; Jan. 1998; 11 Pages.

Thomas, et al.; "Physician Misdiagnosis of Dehydration in Older Adults"; JAMDA; pp. 251-254; Sep./Oct. 2003; 4 Pages.

Thomas, et al.; "Understanding Clinical Dehydration and Its Treatment"; JAMDA; pp. 292-301; Jun. 2008; 10 Pages.

Thornton; "Thirst and hydration: Physiology and consequences of dysfunction"; Physiology & Behavior; pp. 15-21; Jan. 2010; 7 Pages.

Tondare, et al; "Multi-frequency Bioimpedance Monitoring Technique using Network Analyzer for Body Composition Analysis"; International Journal of Engineering Research & Technology; vol. 1; Issue 6; Aug. 2012; 6 Pages.

Rothlingshofer, et al.; "Monitoring Change of Body Fluid during Physical Exercise using Bioimpedance spectroscopy and Finite Element Simulations"; J Electr Bioimp; vol. 2; pp. 79-85; Dec. 7, 2011; 7 Pages.

Tseng, et al.; "In vivo determination of skin near-infrared optical properties using diffuse optical spectroscopy"; Journal of Biomedical Optics 13(1); Jan./Feb. 2008; 7 Pages.

Valle, et al.; "Optimizing fluid management in patients with acute decomposed heart failure (ADHF): the emerging role of combined measurement of body hydration status and brain natriuretic peptide (BNP) levels"; Heart Fail Rev; pp. 519-529; Jan. 2011; 12 Pages.

Van der Wal, et al.; "Compliance in heart failure patients: the importance of knowledge and beliefs"; European Heart Journal 27; pp. 434-440; Jan. 2006; 7 Pages.

Vidale, et al.; "Survival After Multiple Hospitalizations for Infections and Dehydration in Nursing Home Residents with Advanced Cognitive Impairment"; JAMA; vol. 310; No. 3; pp. 319-320; Jul. 17, 2013; 2 Pages.

Vivanti, et al.; "Developing a quick and practical screen to improve the identification of poor hydration in geriatric and rehabilitative care"; Archives of Gerontology and Geriatrics; pp. 156-165; Jan. 2010; 30 Pages.

Wang, et al; "Bluetooth Indoor Positioning using RSSI and Least Square Estimation"; No Date Known; 5 Pages.

Wang, et al.; "High-Precision RSSI-based Indoor Localization Using A Transmission Power Adjustment Strategy for Wireless Sensor Networks"; IEEE 14th International Conference on High Performance Computing and Communications; Jan. 2012; 5 Pages.

Warren, et al.; "The Burden and Outcomes Associated with Dehydration among US Elderly, 1991"; American Journal of Public Health; vol. 84; No. 8; pp. 1265-1269; Aug. 1994; 5 Pages.

Weinberg, et al.; "Dehydration; Evaluation and Management in Older Adults"; JAMA; vol. 274; No. 19; Nov. 15, 1995; 5 Pages.

Wescor; "VAPRO Vapor Pressure Osmometer"; Model 5520; Jan. 1997; 4 Pages.

Wuerz, et al.; "Effects of Prehospital Medications on Mortality and Length of Stay in Congestive Heart Failure"; Annals of Emergency Medicine; Jun. 1992; 6 Pages.

Xiao, et al.; "Economic burden of dehydration among hospitalized elderly patients"; Am J Health-Syst Pharm—vol. 61; pp. 2534-2540; Dec. 1, 2004; 8 Pages.

Xin, et al.; THz Thermal Radiation Enhancement Using an Electromagnetic Crystal; IEEE transactions on Antennas and Propagation; vol. 56; No. 9; Sep. 2008; 11 Pages.

* cited by examiner

NON-INVASIVE SKIN CONTACT SENSOR

CROSS REFERENCE

This Application claims benefit of U.S. Provisional Application 62/786,652, filed Dec. 31, 2018 and entitled "NON-INVASIVE SKIN CONTACT SENSOR", the entire contents of which are incorporated by reference herein.

STATEMENT REGARDING FEDERALLY SPONSORED RESEARCH

This invention was made with government support under U54EB015408 awarded by the National Institutes of Health. The government has certain rights in the invention.

TECHNICAL FIELD

This disclosure relates generally to a hydration sensing and, more particularly, to a tracking a hydration status of a measured tissue.

BACKGROUND

In the field of patient care, patients may become dehydrated easily and frequently, leading to a major contributing factor to poor health and reduced quality of life. Current hydration sensors include no reliable assessment or measurement method sensitive enough to track the small and slow changes in hydration status.

Current hydration sensing technologies such as measurement of body weights and in-out tracking of fluids, aim to provide hydration assessment, but are not accurate enough to track chronic trends of dehydration. Further, hydration sensing technologies such as blood analysis are neither sufficiently sensitive nor practical for daily tracking, and so often dehydration is identified retrospectively in patients after incidents such as orthostatic hypotension-related falls, altered mental status, urinary tract infections, and kidney failure, to name a few.

Another hydration sensing technology, serum osmolality, requires a blood draw and a clinical laboratory. As blood tests cannot reasonably be done as a daily monitoring routine (or at least cannot be easily or conveniently and/or economically be done on a daily basis), the use of blood tests is not practical approach to monitoring hydration levels. Consequently, other hydration sensing technologies monitor other bodily fluids other than water, including urine (osmolality, specific gravity, and/or color) and saliva (osmolality) to determine hydration status. However, even with clinical-lab quality measurements, measuring body fluids other than water provide less sensitive hydration measurements than water and therefore cause difficulty in tracking a user's hydration level for various hydration events such as dehydration.

Bioimpedance spectroscopy is used as a non-invasive electrical measurement for body composition analysis, such as hydration level. However, this approach suffers from variability unless the posture and electrode contact conditions of the bioimpedance spectroscopic sensor are tightly controlled. Further the electrical path must necessarily be long (e.g. often from wrist to ankle), and thus often pass through a gastrointestinal fluid volume which varies significantly with daily activity, thereby making impractical a sensitive measurement of small changes in hydration on a daily basis.

SUMMARY

In accordance with one aspect of the concepts described herein, a method for measuring a change in hydration level in a tissue is provided. The method can comprise placing a first end of a coaxial probe in contact with human tissue. The coaxial probe can be configured to be responsive to radio frequency (RF) signals associated with dielectric spectroscopy. The method can further include exerting a repeatable force (i.e. applying substantially the same force a number of consecutive times) upon a portion of the coaxial probe and radiating an RF signal via the coaxial probe. Also, the method can include detecting, via the coaxial probe, an RF response signal. The RF response signal can be used to determine an amount of liquid within a portion of a tissue. The method can further include determining a change in hydration level for the tissue based upon the determined amount of liquid within the portion of the tissue.

With this particular arrangement, benefits of measuring a change in hydration level are achieved. More particularly, with this technique, relatively small variations in hydration level which occur over a relatively short period of time may be identified, By measuring a liquid using signals associated with dielectric spectroscopy, it is possible to determine an amount of liquid within a tissue by analyzing the frequency response of the tissue to the RF signal applied thereto. Through appropriate selection of a frequency (or a range of frequencies) associated with dielectric spectroscopy, such a frequency response will be substantially limited to, or dominated by, the liquid's electric response. From such a response, an amount of liquid within a portion of the tissue can be determined.

In accordance with one aspect of the concepts, systems and techniques describe herein, it has been recognized that applying a repeatable force to the probe results in measurements which are consistent and reliably repeatable (e.g. the amount of liquid within a tissue may be determined in a substantially consistent manner due to the application of consistent conditions including a force with which the RF probe interacts with a tissue. This allows the hydration level of the tissue to be tracked more accurately than if varying forces were applied (or if no force was applied) to the probe.

Additional features of the concepts, systems and techniques described herein, may include one or more of the following individually or in combination with other features: exerting the repeatable force upon the coaxial probe includes compressing the human tissue; generating an alert based upon a comparison of the determined change in hydration level and a underhydration threshold; monitoring a temperature of the portion of the tissue; determining a change in hydration level for the tissue is further based upon the monitored temperature; storing a determined amount of liquid within the portion of the tissue; determining a change in hydration level for the tissue can include comparing the determined amount of liquid within the portion of the tissue to a previously determined amount of liquid within the portion of the tissue.

Also described is a system for measuring a hydration level in a tissue. The system can include a probe configurable to be in contact with human tissue and to be responsive to signals having a frequency which falls within a range of frequencies suitable for use in dielectric spectroscopy. The system can also include means for exerting a repeatable force upon a portion of the probe and means for radiating a signal through the probe in the spectroscopy frequency range. Further, the system can include signal processing circuitry coupled to said probe. The signal processing circuitry can be configured to determine an amount of liquid within a portion of a human tissue. Also, the system can include means for determining a hydration level for the human tissue based upon the determined amount of liquid within the portion of the tissue.

In embodiments, the probe may be provided as a coaxial probe coupled to a patch. In embodiments the probe is securely coupled to the patch such that application of the patch to human skin causes a first end of the probe to contact human skin. In embodiments, the coaxial probe is responsive to (e.g. is capable of emitting and receiving) signals generated using a spectroscopic technique. Features can include one or more of the following individually or in combination with other features including: the spectroscopic technique can be one of dielectric, near infrared, or infrared spectroscopy; the probe can be either a coaxial probe or fiber optic probe; the probe can include a temperature probe; the system can also include means for generating an alert when the determined hydration level is below an underhydration threshold; the system can also include means for tracking a hydration level for the human tissue; the system can also include means for determining a change in hydration level of the human tissue.

According to another aspect of the concepts described herein, a noninvasive contact sensor for tracking hydration status is disclosed. The sensor can include a probe disposed within a flushed surface housing and configured to measure an amount of liquid within a tissue. Further the sensor can include a force controller coupled to the flushed surfaced housing configured to apply a repeatable force onto the probe.

In embodiments, the probe can emit signals associated with dielectric spectroscopy. In other embodiments, the probe can emit signals associated with infrared spectroscopy.

In embodiments, the sensor can also include a gimbal coupled between the force controller and the flushed surface housing.

In embodiments, the force controller can include a spring while in other embodiments the force controller can include a counterweight.

In accordance with a still further aspect of the concepts described herein, a system for measuring a hydration level in human tissue includes a coaxial probe, a patch coupled to the coaxial probe and configured such that at least a portion of the coaxial probe configured to be in contact with human tissue.

In embodiments, the coaxial probe has a first end configured to be in contact with human tissue and emit and receive signals associated with a spectroscopic technique. In embodiments the coaxial probe has a second end adapted to be coupled to transmit and receive circuitry. In embodiments, the patch is applied with an adhesive. In embodiments, the patch is an adhesive patch. In embodiments, the patch is coupled to the coaxial probe and configured to be adhered to human tissue so as to provide a force upon at least a portion of the coaxial probe configured to be in contact with human tissue. In embodiments the system may further comprise means for receiving signals from the coaxial probe and for determining an amount of liquid within a portion of human tissue in contact with the first end of the probe.

BRIEF DESCRIPTION OF THE DRAWINGS

The concepts, structures, and techniques sought to be protected herein may be more fully understood from the following detailed description of the drawings, in which.

The drawings are not necessarily to scale, or inclusive of all elements of a system, emphasis instead generally being placed upon illustrating the concepts, structures, and techniques sought to be protected herein.

DETAILED DESCRIPTION

Figure 1A:
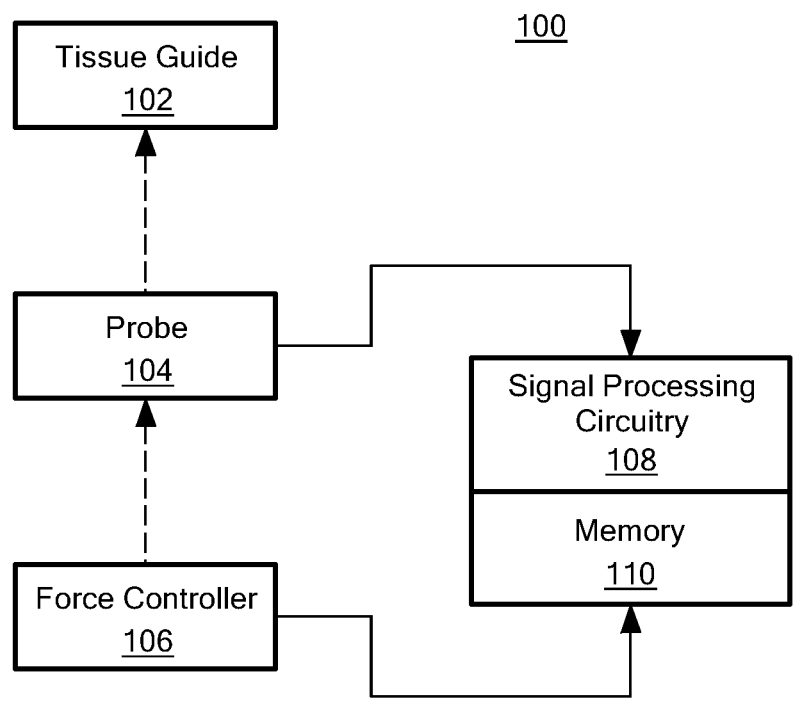
FIG. 1A is a block diagram of a non-invasive skin contact sensor, according to some embodiments.

Referring now to FIG. 1A, noninvasive skin contact sensor 100 is configured to track hydration statuses of at least one user and includes tissue guide 102, probe 104, force controller 106, and signal processing circuitry 108. In embodiments, probe 104 is mechanically coupled to tissue guide 102, force controller 106 and electronically coupled to signal processing circuitry 108.

Probe 104 is configured to perform measurements of at least a portion of a tissue sample of a user. The tissue sample can include a body part from a user such as one or more arms, hands, or fingers. Probe 104 can include a probe configured to perform spectroscopic measurements on at least a portion of a tissue sample such as a coaxial probe (e.g. an open-ended coaxial probe), pump probe, fiber optic probe, Raman probe, or any combination thereof—to name a few examples. In embodiments, probe 104 can be configured to take measurements of a portion of a tissue sample using reflection-based spectroscopy (e.g. dielectric spectroscopy) in a radio frequency (RF) range (e.g. using RF signals in the GHz range), an infrared ("IR") range, near IR range, or any combination thereof.

In embodiments, probe 104 is configured to be in contact with at least a portion of a tissue sample and configured to measure the portion of the tissue sample with which probe 104 is in contact. In some embodiments, at least a portion of probe 104 is configured to be substantially flush with at least a portion the tissue sample.

Probe 104 is configured to take spectroscopic measurements of a liquid within a tissue sample of a user (i.e. using spectroscopy to measure a liquid within a tissue sample). The liquid measured in the tissue sample can include water, blood, plasma, bile, lymph, or any combination thereof—to name a few. For example, probe 104 can be configured to take spectroscopic measurements of water in a tissue sample such as a finger. In embodiments, these measurements can be provided to signal processing circuitry 108 to determine a hydration status of a user.

Probe 104 is configured to perform spectroscopic measurements by emitting low-power signals (e.g. waves, or electric fields), at a predetermined frequency or within a predetermined frequency range in a direction towards a tissue sample of a user. The signals emitted by probe 104 are at frequencies/wavelengths associated with a predetermined spectroscopic technique (e.g. dielectric spectroscopy, near-IR spectroscopy, IR spectroscopy, to name a few.) Frequencies and wavelengths associated with a spectroscopic technique include frequencies and wavelengths of signals suitable for operation, or use, with the spectroscopic technique. For example, signals emitted by probe 104 can have frequencies/wavelengths associated with dielectric spectroscopy (e.g. frequencies between about 1 GHz to about 100 GHz), with near-IR spectroscopy (e.g. wavelengths between about 780 nm to about 2500 nm), with IR spectroscopy (e.g. wavelengths between about 0.8 µm, to about 1000 µm), or any combination thereof—to name a few examples.

The electrical response produced in response to the signals applied in and around the tissue sample is then measured by probe 104. Probe 104 is configured to generate a signal representative of the electrical response induced by the emitted waves. For example, probe 104 can be configured to emit waves associated with dielectric spectroscopy. Probe 104 can generate a signal, as a function of frequency, representative of the electrical response induced by the emitted waves associated with the dielectric spectroscopic technique.

In embodiments, probe 104 can be configured to emit waves at a predetermined frequency associated with a spectroscopic technique while in other embodiments, probe 104 can be configured to emit signals (e.g. waves) within a predetermined range of frequencies associated with spectroscopy techniques such as dielectric spectroscopy (e.g. from 1 to 30 GHz).

By emitting signals (waves) associated with dielectric spectroscopy, probe 104 is configured to measure the electrical coupling between the emitted waves and the liquid within a tissue sample. In the dielectric range, the electrical coupling between the emitted waves and liquid is directly and specifically related to fractional liquid content within the tissue sample. As an example, probe 104 can be configured to take dielectric spectroscopic measurements of water within a tissue sample, because the permittivity of water is ten times greater than other tissue constituents; the coupling between the emitted waves and water within the tissue sample dominates the electrical response. With dielectric spectroscopy, measurements taken of a liquid in a tissue sample are insensitive to electrolytes present with the tissue sample (e.g. calcium, chloride, magnesium, phosphorus, potassium, sodium, etc.).

Unlike measurements taken using signals associated with bio-impedance spectroscopy (e.g. using signals in the frequency range of 1 to 1000 kHz), measurements taken using signals associated with dielectric spectroscopy (e.g. using signals in the frequency range of 1 to 30 Ghz) are substantially insensitive to the electrical conduction between probe 104 and the tissue sample. Also, in the dielectric range, the electric field distribution within tissue sample is substantially localized to a volume under probe 104.

As another example, probe 104 is configured to perform measurements using signals associated with near-IR or IR spectroscopy (i.e. signals with wavelengths between about 780 nm and about 2500 for near-IR and about 0.8 µm to about 1000 µm for IR). In embodiments, probe 104 can be configured to emit signals having a predetermined frequency associated with near-IR or R range spectroscopy, while in other embodiments, probe 104 can be configured to emit signals having varying frequencies within a predetermined frequency range (e.g. a swept signal) of frequencies associated with near-IR or IR spectroscopy.

According to some embodiments, coaxial probe includes a temperature probe. The temperature probe can include AC and/or DC circuitry configured to configured to measure a temperature of the tissue sample. For example, the temperature probe can be configured to measure the temperature of the skin of a finger. In embodiments, measurements taken by the temperature probe are provided to signal processing circuitry 108.

In some embodiments, probe 104 is mechanically coupled to tissue guide 102. Tissue guide 102 is configured to receive at least a portion of a tissue sample of a user to be measured by probe 104. In embodiments, tissue guide 102 can include a housing comprised of one or more of plastic (e.g. polyethylene, polyvinyl chloride, acrylic, etc.), metal (e.g. stainless steel, steel, iron, titanium, etc.), carbon fiber, either singly or in any combination of such materials. Other materials may, of course, also be used. In embodiments, the housing is configured so that at least a portion of a tissue sample may be inserted. The housing can include an opening of sufficient size, area, or volume to allow the portion of the tissue sample to be inserted. For example, the housing may have an opening of sufficient volume as to allow at least a portion of a user's finger to be inserted.

In embodiments, tissue guide 102 is configured so that when a portion of a tissue sample is received, the portion of the tissue sample comes into contact with probe 104. For example, tissue guide 102 can be configured so that when a portion of a finger is placed on the guide (i.e. the tissue sample is received), the finger comes into contact with tissue sample 104. In embodiments, tissue guide 102 is configured to have an angle, shape, area, volume, surface area, or any combination thereof, of sufficient degrees so that a received portion of a tissue sample comes into contact with probe 104. For example, tissue guide 102 can be configured to have a shape and angle of sufficient size so that when a portion of finger is received, the portion of the finger comes into contact with probe 104. In embodiments, tissue guide 102 is configured so that at least a portion of the tissue sample lies flush with probe 104.

In embodiments, because of positional differences in tissue sample properties (e.g. fractional liquid content, thickness, composition, or any combination thereof—to name a few), tissue guide 102 can be configured so that predetermined locations, or portions, of a tissue sample are measured. In other words, tissue guide 102 can be configured so that only predetermined locations of a tissue sample of a user are measured by probe 104. For example, tissue guide 102 can be configured so that only a predetermined location of a user's fingers is measured by probe 104. In embodiments, tissue guide 102 can include angles, shapes, areas, volumes, surface areas, or any combination thereof, of sufficient degrees so that only predetermined locations of a tissue sample of a user come into contact with probe 104.

In embodiments, noninvasive skin contact sensor 100 includes force controller 106 mechanically coupled to probe 104. Force controller 106 is configured to apply a repeatable force onto at least a portion of probe 104 so that probe 104, in turn, applies a repeatable force to at least a portion of the tissue sample of a user in contact with probe 104. By applying a repeatable force, substantially the same force can be repeated for a predetermined, or specific tissue sample each probe 104 performs a measurement.

For example, a force that can be repeatedly applied to a tissue sample (such as a finger) belonging to a specific user. Thus, for a specific user, substantially the same force is applied to a particular tissue sample (e.g. the same force is applied each time the same portion of the same finger is used). It should, of course, be appreciated that other body parts may be used to determine hydration levels and that the guide and/or probe and/or other structures of sensor 100 may be suitably modified as needed to accept particular body parts.

Applying a substantially repeatable force to a portion probe 104 (and thus to the portion of the tissue sample in contact with probe 104) aids in ensuring the exudation of other liquids within the tissue sample that may interfere with measurements. For example, probe 104 may be configured to measure water in at least a portion of a tissue sample. Here, applying a repeatable force to probe 104 aids in ensuring the exudation of blood from capillaries in a tissue sample, which reduces the potential for unreliable measurements due to variation in capillary distribution and vasodilation due to significantly higher water content in blood than the surrounding tissue sample.

Further, applying a substantially repeatable force to probe 104 aids in ensuring that the measurements taken by probe 104 are substantially consistent. That is to say, applying a substantially repeatable force to probe 104 helps to ensure that a tissue sample is in a substantially consistent state (e.g. substantially consistent pressure on the tissue sample, portion of the tissue sample measured, exudation of other liquids within the tissue sample, etc.) each time that probe 104 takes a measurement.

In embodiments, force controller 106 may apply a repeatable force to probe 104 via gravity (such as, for example, by a counterweight, counter balance, etc.), a spring mechanism, electromagnet actuation (such as a servo motor), a wristband, an armband, or any combination thereof, to name a few examples.

In some embodiments, force controller 106 can apply a predetermined amount of force to probe 104 every time probe 104 is to take a measurement of a tissue sample. For example, force controller 106 can apply a predetermined amount of force to probe 104 via a servo motor or counterweight every time probe 104 is to take a measurement of a tissue sample. One of skill in the art will appreciate that a predetermined force can be applied through the design of force controller 106 (such as through programming of a servo motor, design of a counter balance, or any combination thereof—to name a couple examples).

In other embodiments, force controller 106 can apply a respective repeatable force for each tissue sample that is to be measured. In other words, force controller 106 can apply a respective repeatable force that depends upon, but is not limited to, the size, density, volume, surface area—or any combination thereof—of a tissue sample each time that respective tissue sample is measured. To apply the respective repeatable forces, controller 106 can include a spring mechanism, an armband, a wrist band, or any combination thereof.

In embodiments, measurements (i.e. spectroscopic measurements and/or temperature measurements) taken by probe 104 are provided to signal processing circuitry 108. Signal processing circuitry 108 can include a computer, a digital signal processor ("DSP"), microprocessor, network, database, or any combination thereof. Signal processing circuitry 108 is configured to determine a hydration content for the tissue sample according to the spectroscopic measurements taken by probe 104. In embodiments, such as when probe 104 emits signals associated with dielectric spectroscopy, the measurements provided from probe 104 to signal processing circuitry 108 may be represented as a function of frequency.

In embodiments, signal processing circuitry 108 is configured to determine a fractional liquid content in a tissue sample based upon the measurements taken by probe 104. For example, signal processing circuitry 108 can be configured to perform operations on the received measurements from probe 104 to determine a fractional liquid content, or percentage, of liquid in a measured tissue sample. In embodiments, signal processing circuitry 108 can be further configured to determine a hydration level for a user based upon the fractional liquid content determined for the tissue sample. For example, signal processing circuitry 108 can be configured to determine a fractional water content in a tissue sample such as a dermis based upon measurements taken by probe 104 and can further determine a hydration status of a user based upon the determined fractional water content.

In embodiments, signal processing circuitry 108 is configured to adjust a determined hydration status according to the temperature measurements taken by probe 104. For example, the hydration status can be adjusted to correct for environmental/physiological phenomena, like low peripheral blood flow in cold environments.

In embodiments signal processing circuitry 108 includes a vector network module configured to perform operations on measurements received form probe 104. For example, the vector network module can be configured to determine the magnitude and phase of measurements provided to signal processing circuitry 108 as a function of time (such as when probe 104 emits signals associated with dielectric spectroscopy.

In embodiments, signal processing circuitry 108 includes memory 110. Memory 110 is configured to store fractional liquid contents and hydration levels determined by signal processing circuitry 108. Memory 110 can include a flash memory, read-only memory ("ROM"), programmable ROM ("PROM"), electronically erasable PROM ("EEPROM"), a hard drive, or any combination thereof—to name a few.

In embodiments, signal processing circuitry 108 can associate identification information with the determined fractional liquid contents and hydration levels when they are stored in memory 110. Identification information can include, but is not limited to, data identifying a particular user, data indicating a timing such as, but not limited to, time of day, date, day of the week—any combination thereof—of when a fractional liquid content and/or hydration level was determined, data identifying a noninvasive skin contact sensor used to take measurements of a user, or any combination thereof. Associating determined fractional liquid contents and/or hydration levels with identification information can include storing the data in the same table, storing data in the same column, storing data in the same row, associating the data with pointers, or any combination thereof, to name a few examples.

In embodiments, signal processing circuitry 108 is further configured to track a hydration status of a user according to data stored in memory 110. A hydration status can include a comparison of a hydration status associated with a user compared to a underhydration threshold (e.g. a level of hydration indicating a user is dehydrated), a comparison of a user's hydration status compared to an overhydration threshold (e.g. a level of hydration indicating a user is overhydrated), a change in hydration level, or any combination thereof—to name a few examples. In embodiments, signal processing circuitry 108 is configured to determine a change in hydration level for a user based upon determined hydration levels stored in memory 110. Determining a change in hydration level can include comparing a most recent determined hydration level for a user to at least one of a previous determined hydration level of a user, comparing stored determined hydration levels determined during a predetermined amount of time (e.g. comparing hydration levels determined during a predetermined amount of hours, days, weeks, years, or any combination thereof), comparing stored determined hydration levels to an underhydration and/or overhydration threshold, or any combination thereof.

Signal processing circuitry 108 can further compare a determined change in hydration level to an underhydration change threshold (e.g. a change in hydration level indicating a user is dehydrated) and/or an overhydration change threshold (e.g. a change in hydration level indicating a user is overhydrated). Based upon the comparison, signal processing circuitry 108 can generate an alert indicating that a user is dehydrated based upon the comparison of the change in hydration level to the underhydration change threshold and/or generate an alert indicating that a user is overhydrated based upon the comparison of the change in hydration level to the overhydration change threshold. An alert can include a signal indicating underhydration and/or overhydration, an alarm, an audio prompt indication underhydration and/or overhydration, a visual prompt indicating underhydration and/or over hydration, or any combination thereof—to name a few examples.

Figure 1B:
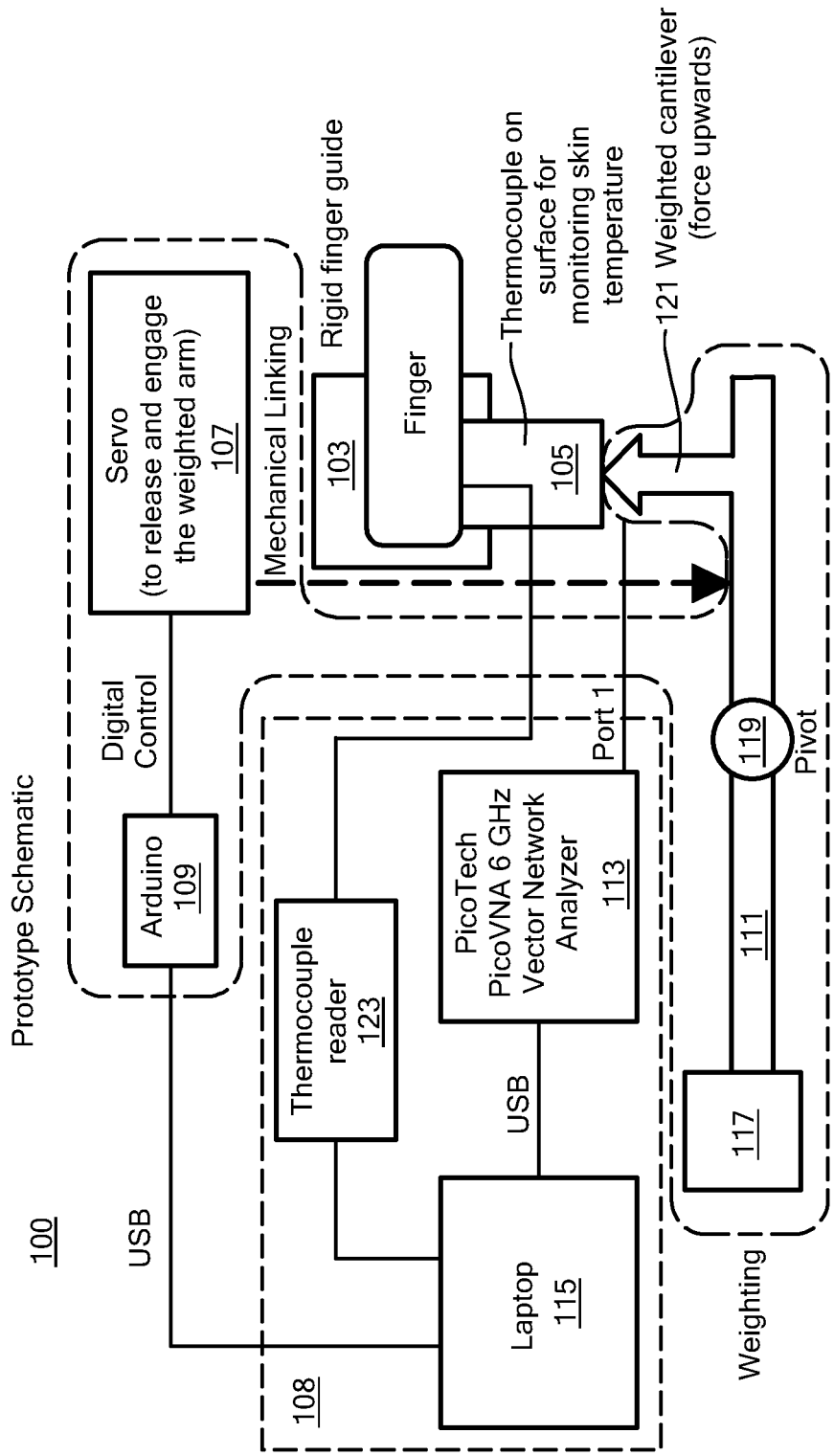
FIG. 1B is a block diagram of an example non-invasive skin contact sensor, according to an illustrative embodiment.

Referring now to FIG. 1B, an illustrative embodiment of a noninvasive skin contact sensor is provided. According to this illustrative embodiment, noninvasive skin contact sensor 100 includes tissue guide 102 (here represented as rigid finger guide 103), probe 104 (here represented as coaxial probe 105), force controller 106 (here represented as including servo 107, microcontroller 109, and counter weight 111), and signal processing circuitry 108 (here represented as including microcontroller 113, laptop 115, and thermocouple reader 123).

In the illustrative embodiment of FIG. 1B, a finger of a user can be received by finger guide 103, which in some embodiments is rigid. Finger guide 103 can include a housing the same or similar as the housing of tissue guide 102 as discussed above with reference to FIG. 1A. As the user's finger is inserted into finger guide 103, at least a portion of the user's finger is brought into contact with coaxial probe 105. In embodiments, finger guide 103 is configured so that at least a portion of the user's finger is flush with coaxial probe 104.

Coaxial probe 105 includes a coaxial termination within a flushed surface housing. The housing can include plastic (e.g. polyethylene, polyvinyl chloride, acrylic, etc.), metal (e.g. stainless steel, steel, iron, titanium, etc.), carbon fiber, either singly or in any combination of such materials. Other materials may, of course, also be used. The coaxial termination of coaxial probe 105 is configured to be substantially flush with the housing.

Force controller 106 is configured to apply a repeatable force onto coaxial probe 105. Force controller 106 includes counterweight 111 including weighting 117, pivot 119, and weighted cantilever 121. The repeatable force applied by counterweight 111 is determined by weighting 117. Weighting 117 includes a weight applied at a first end of counterweight 111. In other words, weighting 117 applies a gravitational force in a first direction (e.g. down) on a first end of counterweight 111. One of skill in the art will appreciate that the appreciate that a desired repeatable force may be achieved according to the values of the weights chosen for weighting 117.

As the weight is applied at the first end of counterweight 111, counterweight 111 pivots at pivot 119 causing weighted cantilever 121 to apply a repeatable force onto coaxial probe 105 in a direction opposite of the gravitational force applied by weighting 117. Due to pivot 119, the repeatable force applied by weighted cantilever 121 is substantially equal to the gravitational force applied by weighting 117. Because the repeatable force is determined by weighting 117, a substantially equal force will be applied to coaxial probe 105 each time coaxial probe 105 performs measurements a user's finger.

Force controller 106 further includes servo 107 and microcontroller 109. Servo 107 is configured to apply a force onto weighted cantilever 121 in a direction opposite of the repeatable force applied by weighted cantilever 121 so that weighted cantilever 121 applies no force onto coaxial probe 105.

In embodiments, microcontroller 109 can be configured so that when a finger in received by rigid finger guide 103, a signal is sent to servo 107 to release counterweight 111. In other words, microcontroller 109 can be configured to generate a signal indicating to servo 107 to stop applying a force to weighted cantilever 121 so that weighted cantilever 121 can apply the repeatable force to coaxial probe 105.

In embodiments, signals representative of the spectroscopic measurements performed by coaxial probe 105 may be provided to microcontroller 113 and temperature measurements performed by coaxial probe 105 may be provided to thermocouple reader 123. Microcontroller 113 can include a vector network analyzer and is configured to determine a hydration status for a user as discussed above with reference to FIG. 1A. The vector network analyzer can be configured to measure the phase and magnitude of the signals representative of the measurements performed by probe 104.

Figure 2:
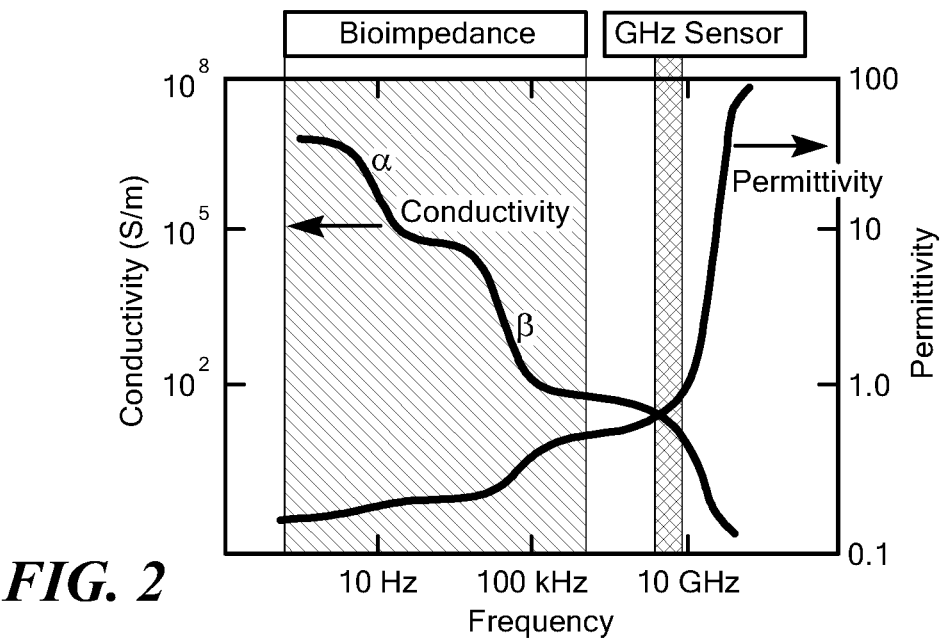
FIG. 2 is a plot representing the electrical responses of permittivity and conductivity of water within a tissue sample vs the frequency of waves emitted, according to some embodiments.

Referring now to FIG. 2, a plot representing the electrical responses of permittivity and conductivity of water within a tissue sample vs the frequency of waves emitted by probe 104 is provided.

Figure 3:
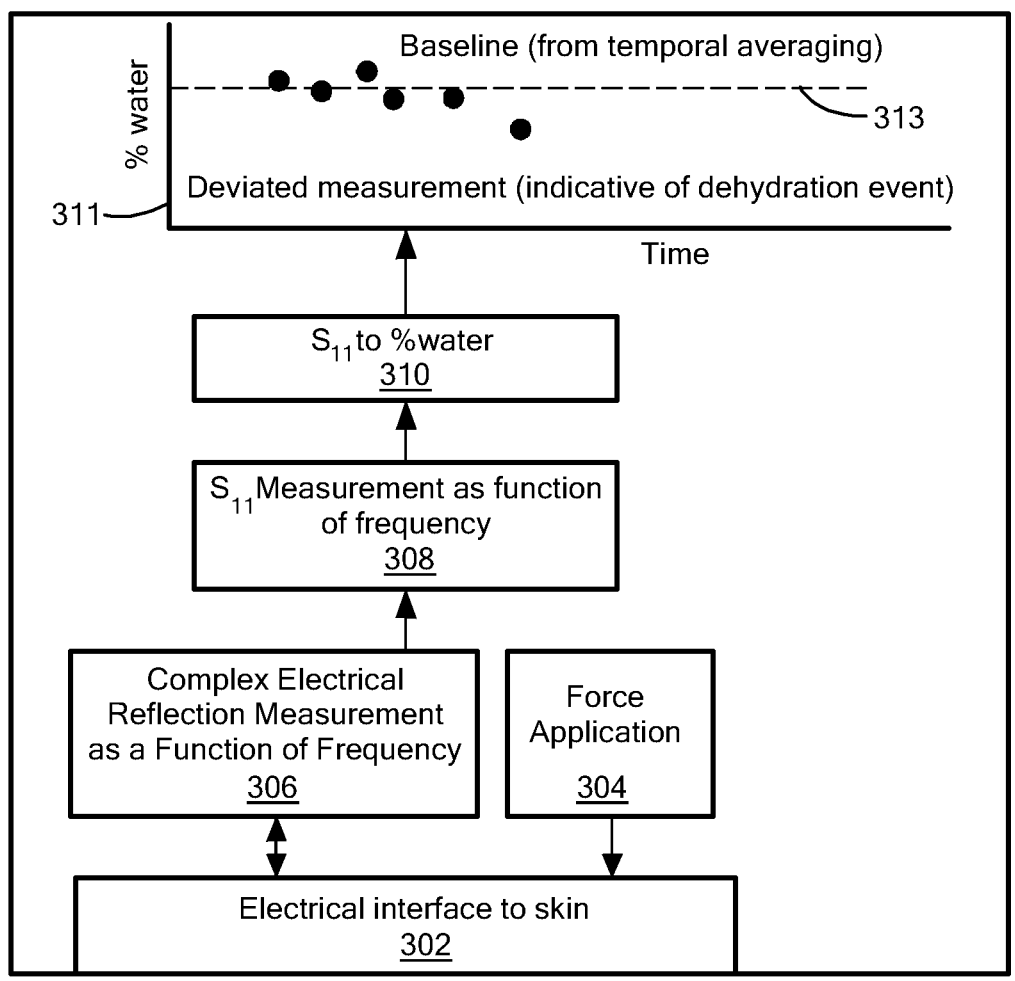
FIG. 3 is a measurement schematic for measuring hydration of a tissue sample, according to some embodiments.

Referring now to FIG. 3, an illustrative embodiment of a measurement schematic is provided. At 302, a probe-tissue interface is applied to the skin of a user. The probe-tissue interface includes a probe the same or similar as probe 104 as discussed above with reference to FIG. 1A. At 304, a repeatable force is applied to the electrical interface 302. In embodiments, the repeatable force can be applied to the electrical interface by force controller 106, as discussed above with reference to FIG. 1A.

At 306, spectroscopic measurements of the skin of the user are taken through the electrical interface, such as the measurements taken by probe 104 as discussed above with reference to FIG. 1A. At 308, probe-tissue interface 302 provides response signals to signal processing circuitry which may be the same as or similar to signal processing circuitry 108 discussed above with reference to FIG. 1A. In embodiments, the measurements may be provided to the signal processing circuitry as a function of frequency (e.g. as reflection coefficient values $S_{11}$).

At 308, the signal processing circuitry the same or similar as signal processing circuitry 108 determines a hydration level for the user based upon the signals representative of the spectroscopic measurements, as discussed above with reference to FIG. 1A. At 310, the signal processing circuitry tracks the user's hydration level as discussed above with reference to FIG. 1A.

Plot 311 represents a user's hydration level (in % water) over time. As can be seen from plot 311, a user's hydration level remains around a hydration baseline 313 before falling below the baseline. A hydration baseline can include the average hydration for a user over a predetermined amount of time. In embodiments, the hydration baseline can be used as an underhydration threshold or an overhydration threshold to determine if a user is underhydrated or overhydrated, respectfully, as discussed above with reference to FIG. 1A. For example, in plot 311, as the hydration level falls below the hydration baseline, the change in hydration level indicates underhydration, or dehydration, of the user.

Figure 4:
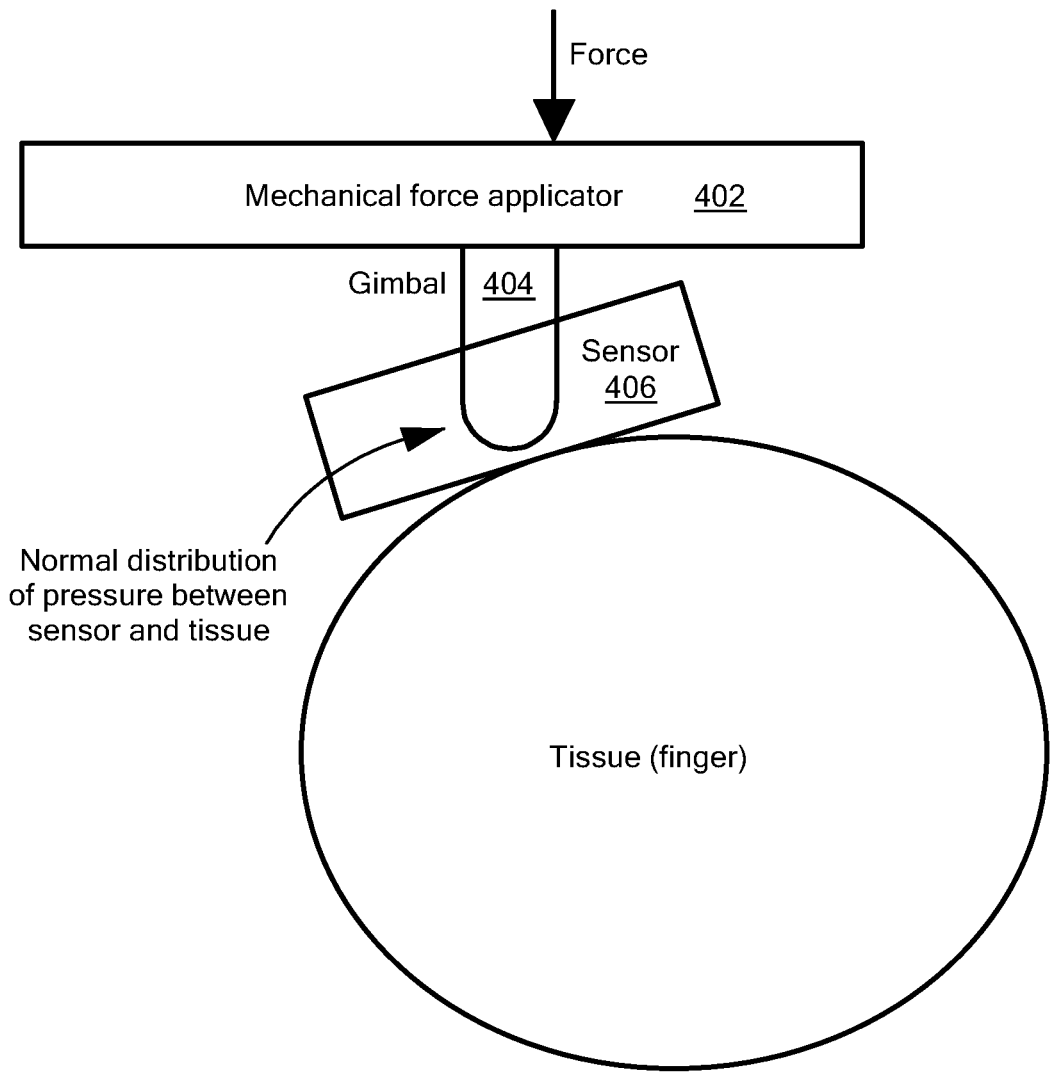
FIG. 4 is a block diagram of a force controller, according to some embodiments.

Referring now to FIG. 4, a force controller which may be the same as or similar to force controller 106 discussed above with reference to FIG. 1A can include mechanical force applicator 402 and gimbal 404. The force controller can be configured to apply a repeatable force to probe 406 (probe 406 may be the same as or similar to probe 104 discussed above with reference to FIG. 1A). As the repeatable force is applied to probe 406, probe 406 in turn applies force to a tissue sample (here represented as tissue sample 408).

Mechanical force applicator 402 is configured to apply a force to probe 406 and can include a counterweight, a spring mechanism, an armband, a wristband, a servo motor, or any combination thereof—to name a few examples. In embodiments, gimble 404 may be mechanically coupled between mechanical force applicator 402 and probe 406. In embodiments, the gimble may be configured so that the repeatable force applied to probe 406 causes a normal distribution of pressure between probe 406 and tissue sample 408. In other words, gimble 404 is configured to apply the repeatable force to probe 406 at an angle so that there is a normal distribution of pressure between probe 406 and tissue sample 408. Without gimble 404, the repeatable force may be applied to probe 406 so that there is a nonuniform distribution of pressure between probe 406 and tissue sample 408 which may lead to inaccurate measurements taken by probe 406.

Figure 5A:
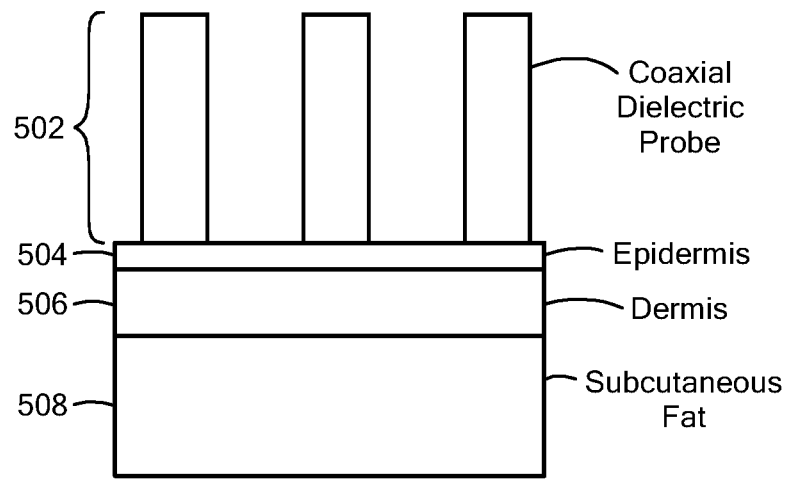
FIGS. 5A and B are diagrams of an example tissue sample, according to an illustrative embodiment.
Figure 5B:
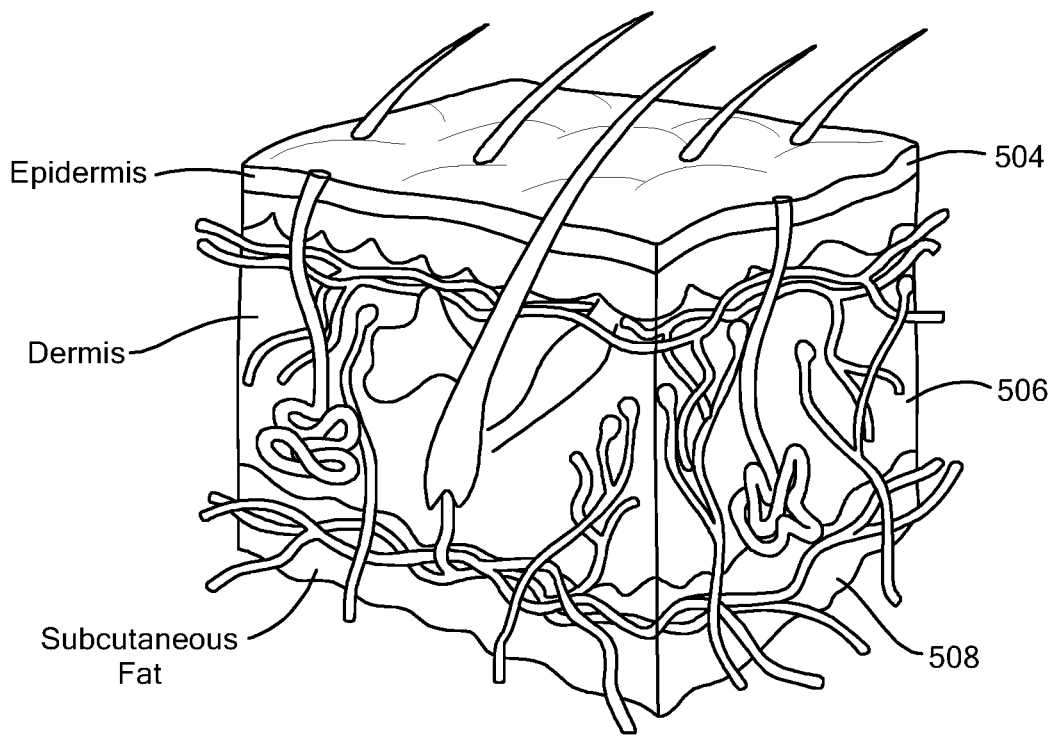

Referring now to FIGS. 5A and B, an example of a tissue sample is provided. In an illustrative embodiment, probe 502, which may be the same or similar to probe 104 described above with reference to FIG. 1A, is configured to take spectroscopic measurements of a tissue sample that includes epidermis 504, dermis 506, subcutaneous fat 508. In embodiments, epidermis 504, dermis 506, subcutaneous fat 508 can comprise layers of a user's finger that is to be measured by probe 502.

In embodiments, probe 502 is configured to lie flush on at least a portion of epidermis 504 of the tissue sample.

Figure 6:
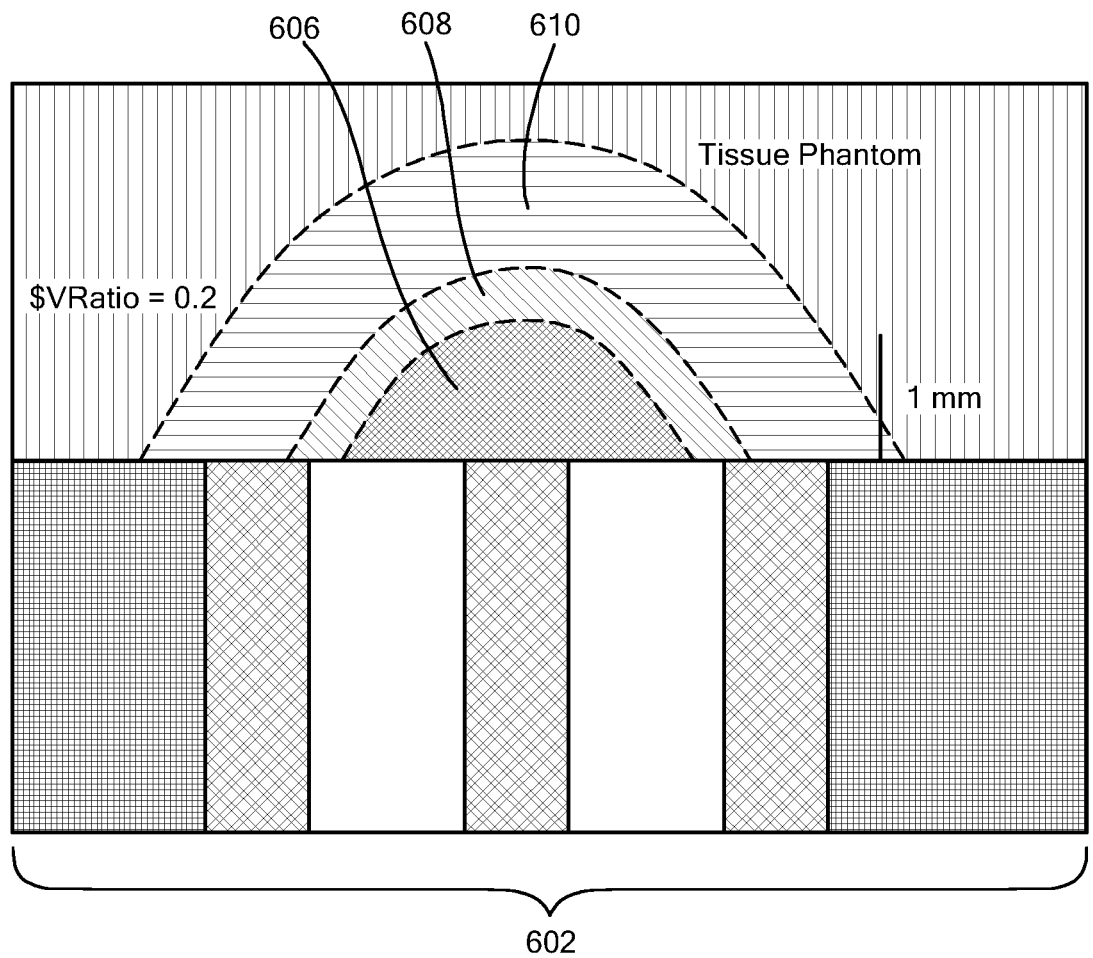
FIG. 6 is a plot of a simulated electrical field intensity is provided, according to an illustrative embodiment.

Referring now to FIG. 6, a simulated electric field intensity is shown. In embodiments, probe 602 (which is the same or similar as probe 104 as discussed above with reference to FIG. 1A) is configured to perform spectroscopic measurements of a tissue sample. As probe 602 emits signals (e.g. EM waves) at a predetermined frequency or within a predetermined range of frequencies, an electrical response is induced in the tissue sample. The electrical response may correspond to a high intensity electrical field 606 in the tissue sample. In embodiments, the high intensity electrical field may exist through a distance of 1 mm above a surface of the tissue. The electrical response further includes a moderate intensity electrical field 608 and a low intensity electrical field 610.

As can be seen from FIG. 6, high intensity electrical field 606 and moderate intensity field 608 are induced in the tissue sample relative to the location of probe 602. In embodiments, high intensity electrical field 606 represents an effective sample volume for probe 602 as probe 602 performs spectroscopic measurements.

Figure 7:
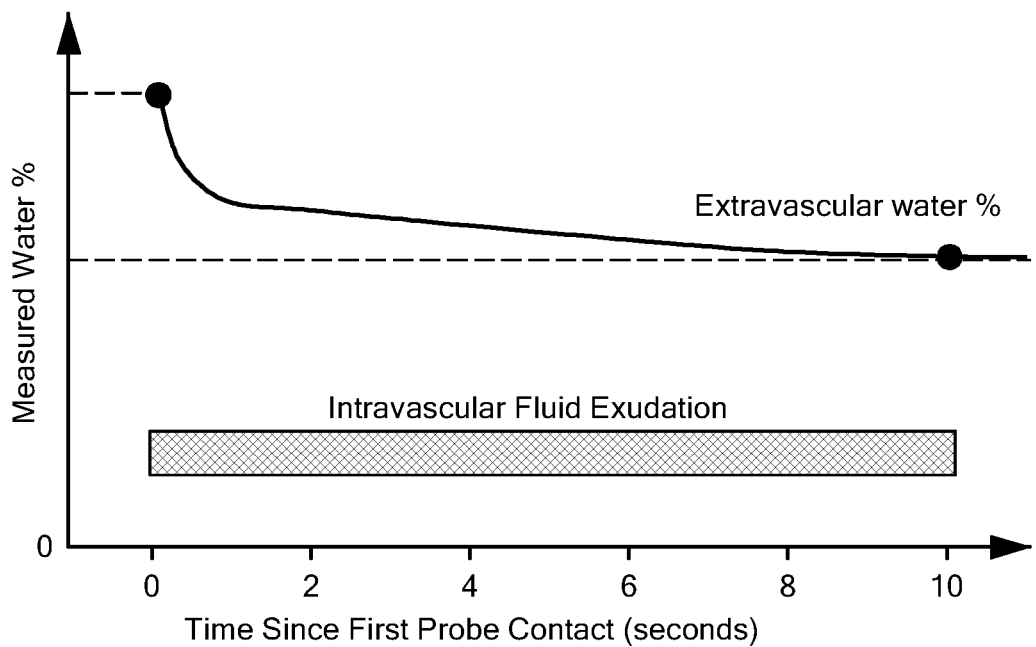
FIG. 7 is a plot representing measured water in a tissue sample (in percentage) vs. time since first probe contact (in seconds), according to some embodiments.

Referring now to FIG. 7, a plot representing measured water in a tissue sample (in percentage) vs. time since first probe contact (in seconds) is provided. At 0 seconds, probe 104 is brought into contact with a tissue sample and a first measured water percentage is determined. After 0 seconds, a repeatable force is applied to probe 104 which vacates blood from the capillaries in a tissue sample. As the blood is vacated due to the repeatable force, the measured water level decreases indicating that only the extravascular water is being measured. As can be seen in the illustrative embodiment of FIG. 7, when the blood is not vacated from the capillaries of the tissue sample, probe 104 measures a higher water level compares to when the blood has been vacated from the capillaries. Because of this, ensuring the exudation of blood from capillaries in a tissue sample reduces the potential for unreliable measurements due to variation in capillary distribution and vasodilation due to significantly higher water content in blood than the surrounding tissue sample.

Figure 8:
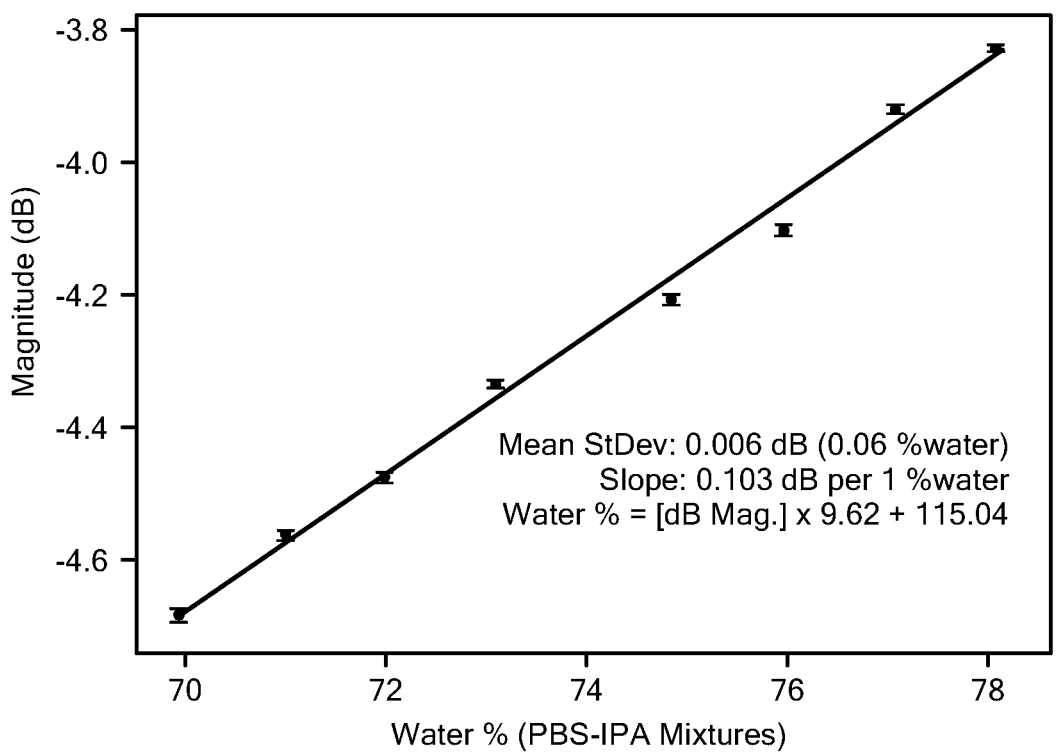
FIG. 8 is an example plot representing the magnitude of a signal representative of measurements taken vs fractional water content of a tissue, according an embodiment.

Referring now to FIG. 8, an example plot representing the magnitude of a signal representative of measurements taken by probe 104 (in dB) vs fractional water content of a tissue sample is provided. As can be seen from the plot in FIG. 8, a sensitivity of 0.11 dB per 1% change in fractional water content is represented. In embodiments, signal processing circuitry 106 can use this sensitivity to determine a hydration level of a user or track a hydration status of a user as discussed above with reference to FIG. 1.

Figure 9B:
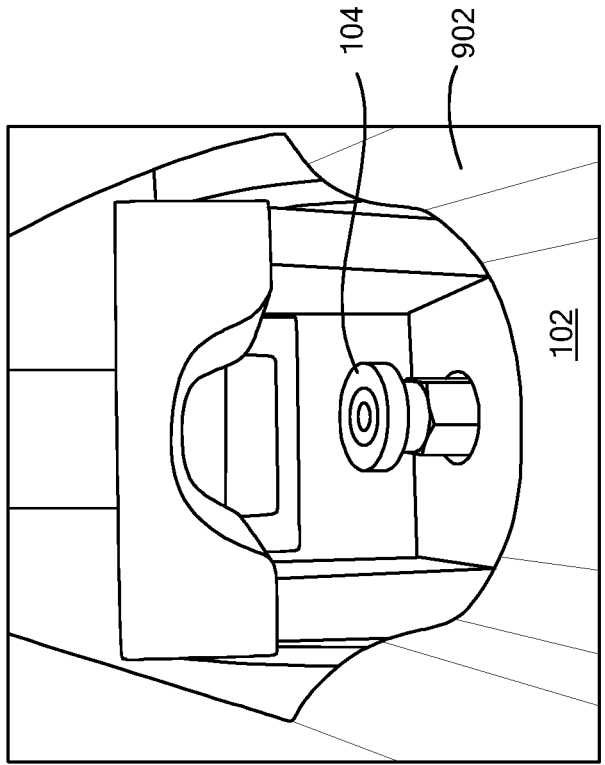
FIGS. 9A-C are illustrations of an example implementation of a noninvasive skin contact sensor, according to an illustrative embodiment.
Figure 9A:
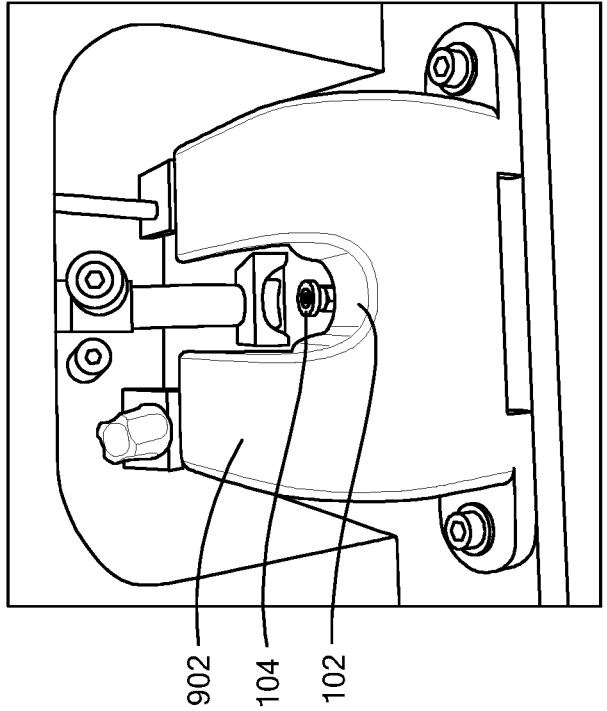
Figure 9C:
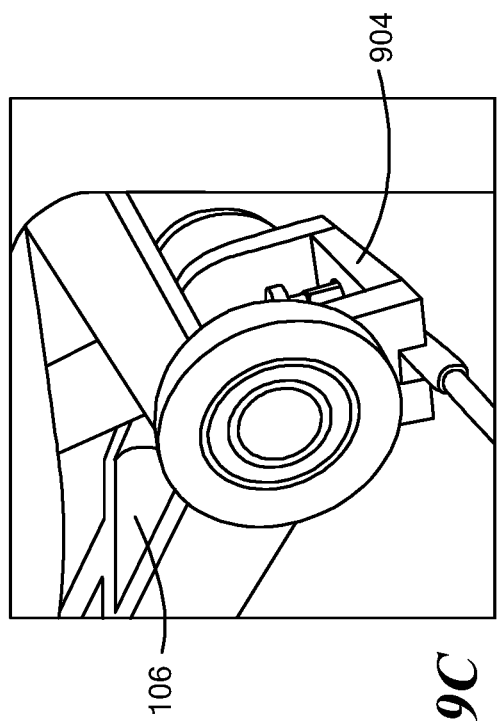

Referring now to FIGS. 9A-C, an example implementation of noninvasive skin contact sensor 100 is provided. In the example implementation, tissue guide 104 includes housing 902. Housing 902 comprises plastic and is configured to allow a user's finger to be inserted so that it makes contact with probe 104.

Probe 104 is configured to take spectroscopic measurements (via a dielectric spectroscopy technique) of at least a portion of a user's finger and further includes a temperature sensor to measure a temperature of at least a portion of the user's finger. Force controller 106 is configured to apply a repeatable force onto probe 104 so that probe 104 applies a force onto at least a portion of the user's finger. Force controller 106 includes a counterweight 904 that is released by a servo motor as discussed above with reference to FIG. 1B.

Figure 10:
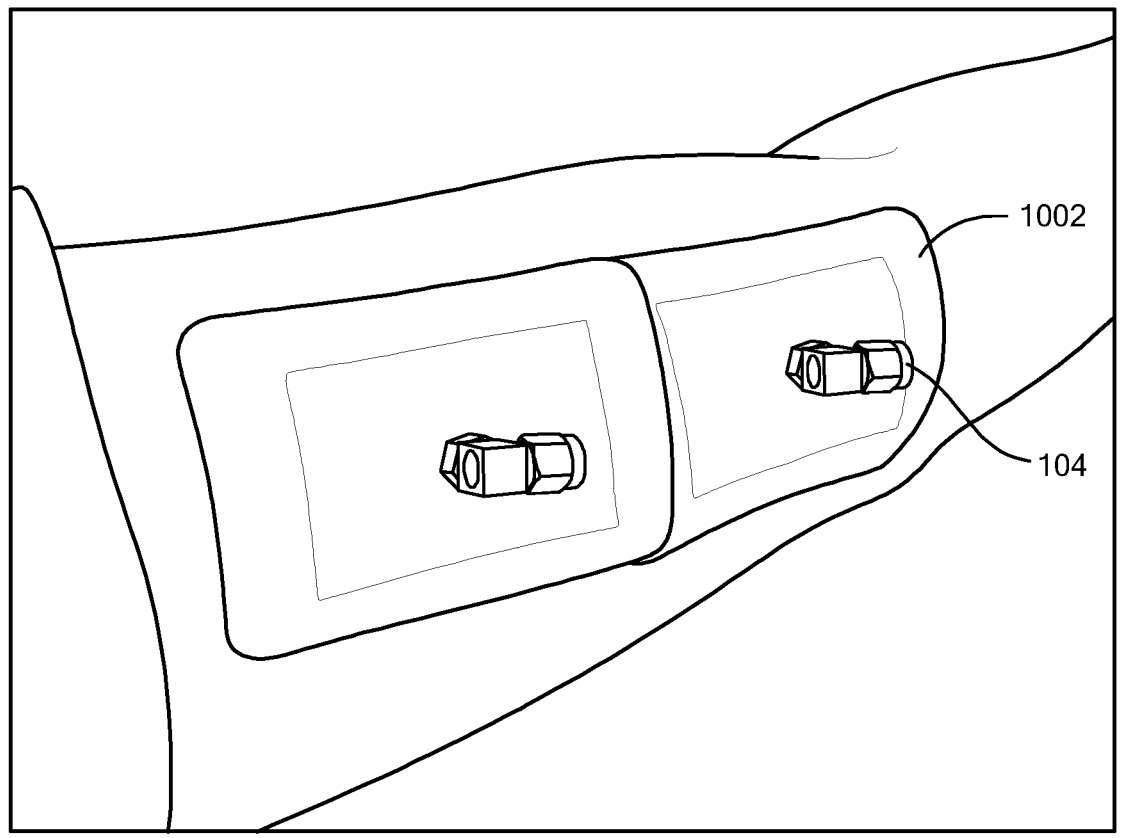
FIG. 10 is an illustration of an example implementation of a noninvasive skin contact sensor, according to an illustrative embodiment.

Referring now to FIG. 10, an example implementation of noninvasive skin contact sensor 100 is provided. In an illustrative implementation, noninvasive skin contact sensor 100 includes probe 104 and force controller 106 represented here as patch 1002. Patch 1002 is configured to apply a force (and ideally a repeatable force) on probe 104 by adhering to at least a portion of a tissue sample (here represented as the arm of a user). As patch 1002 adheres to at least a portion of the tissue sample, a force is applied to probed 104, which in turn, applies a force to the tissue sample. In embodiments, patch 1002 can be adhered to the same predetermined portion of a tissue sample each time probe 104 is to take a measurement. Adhering patch 1002 to the same predetermined portion of the tissue sample helps to ensure that the conditions in which probe 104 takes measurements remain substantially consistent each time probe 104 takes a measurement. For example, adhering patch 1002 to the same predetermined portion of the tissue sample aids in ensuring that a repeatable force is applied and remains substantially consistent across all measurements (as different portions of a tissue sample may vary in size, shape, volume, etc.) and further aids in ensuring that other factors (such as density of veins, capillaries, blood, etc.) within the portion of the tissue sample remain consistent for all measurements.

In embodiments the patch is directly coupled to the coaxial probe and configured such that at least a portion of the coaxial probe (e.g. an end of the coaxial probe) is capable of being in contact with human tissue when the patch is applied.

In embodiments, the coaxial probe has a first end configured to be in contact with human tissue and further configured to emit and receive signals associated with a spectroscopic technique. In embodiments the coaxial probe has a second end adapted to be coupled to transmit and receive circuitry. In embodiments, the patch is applied with an adhesive. In embodiments, the patch comprises an integral adhesive (i.e. the patch is an adhesive patch). In embodiments, the patch is coupled to the coaxial probe and configured to be adhered to human tissue so as to provide a force upon at least a portion of the coaxial probe configured to be in contact with human tissue. The patch and probe may be coupled to means for determining an amount of liquid within a portion of human tissue in contact with a first end of the probe. In embodiments, the means for determining may be coupled to a second end of the probe (e.g. a second opposite end of the coaxial probe) and configured to receive signals from the coaxial probe.

Figure 11B:
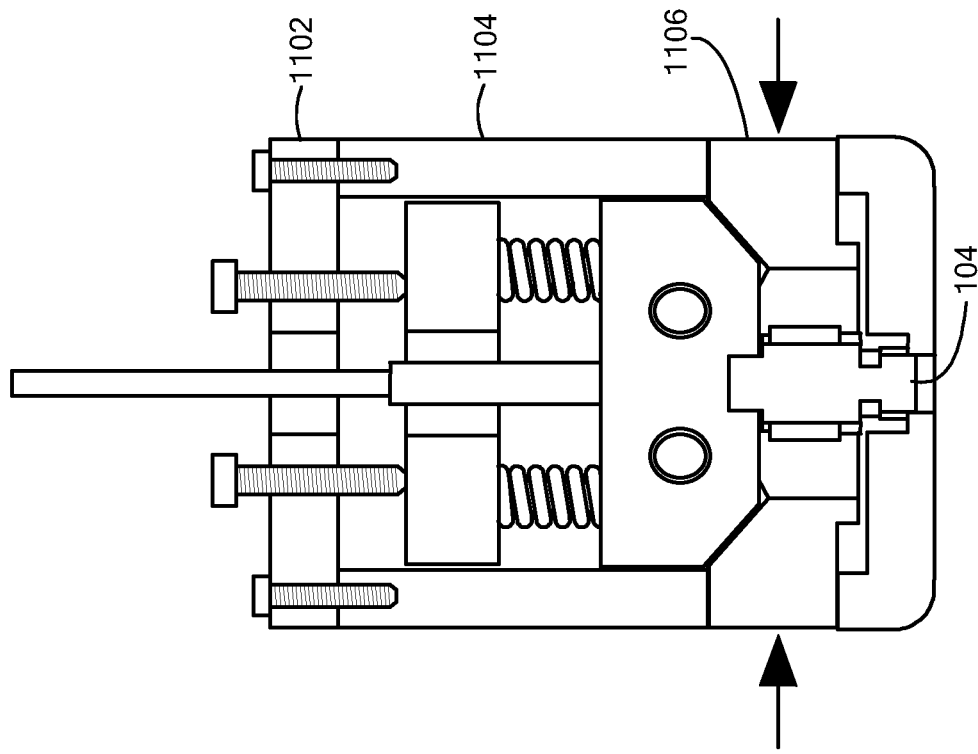
FIGS. 11A-C are illustrations of an example implementation of a noninvasive skin contact sensor, according to an illustrative embodiment.
Figure 11A:
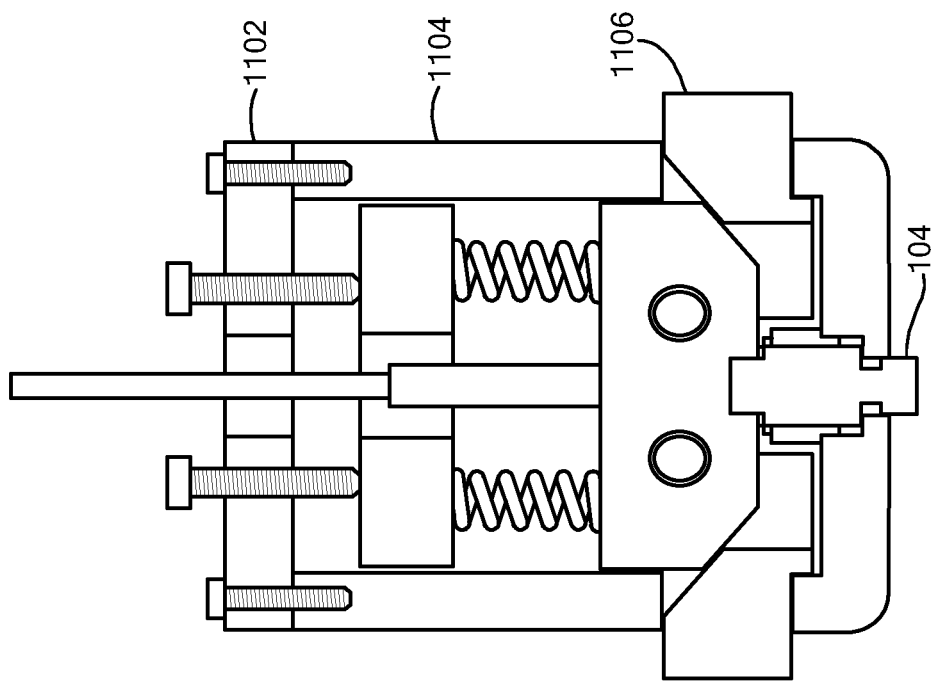
Figure 11C:
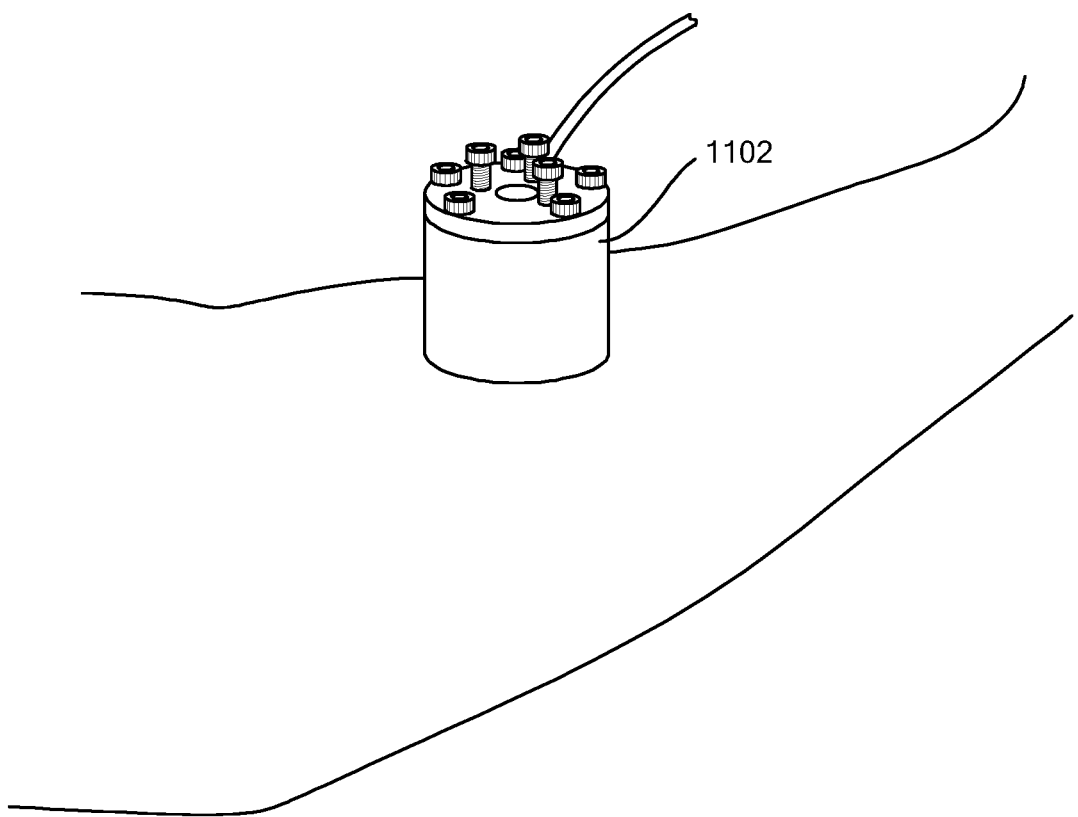

Referring now to FIGS. 11A-C, in which like elements are provided having like reference numerals through the several views, an example implementation of noninvasive skin contact sensor 100 is provided. In an illustrative implementation, noninvasive skin contact sensor 100 includes probe 104 that includes housing 1102 and force controller 106 represented here as spring mechanism 1104. Housing 1102 can be configured to sit flush on a tissue sample, here represented as a user's arm.

Housing 1102 includes mechanical buttons 1106 on opposite sides of housing 1102 to retract spring mechanism 1104 so that probe 104 is substantially flush with housing 1102. Upon releasing the buttons, spring mechanism expands and applies a repeatable force onto probe 104, which in turn, applies a force to the tissue sample.

Figure 12:
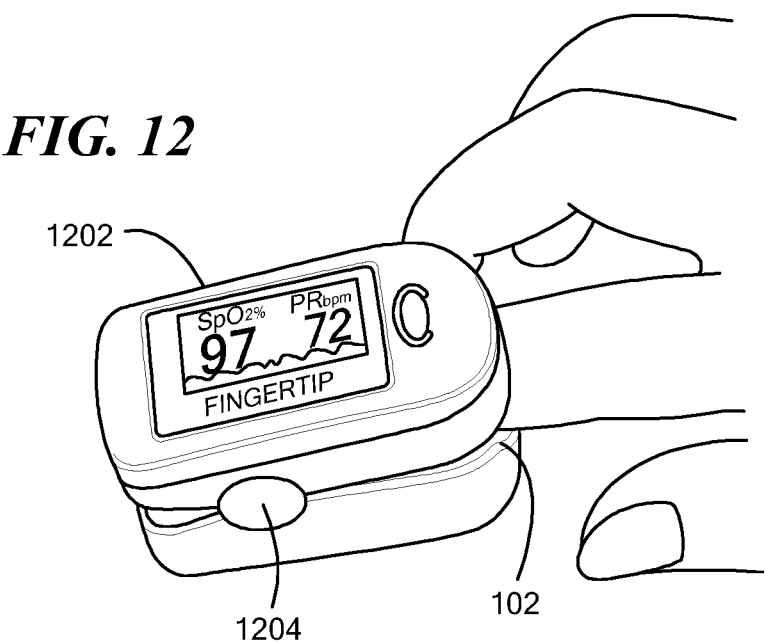
FIG. 12 is an illustration of an example implementation of a noninvasive skin contact sensor, according to an illustrative embodiment.

Referring now to FIG. 12, an example implementation of noninvasive skin contact sensor 100 is provided. In an illustrative implementation, noninvasive skin contact sensor 100 is provided as a modified oximeter and includes tissue guide 102 that includes housing 1202, probe 1206 (not shown) and force controller 106 represented here as spring mechanism 1204. Housing 1202 is configured to receive a tissue sample from a user, here represented as a user's finger. As the tissue sample is received by housing 1202, the tissue sample comes into contact with probe 104. In embodiments, probe 104 can be configured to emit signals associated with IR spectroscopy. In other words, probe 104 can be configured to emit signals with frequencies and wavelengths associated with IR spectroscopy as discussed above with reference to FIG. 1A.

Here, the conventional oxygen saturation probe of a conventional oximeter can be replaced by, or modified to include, probe 104 that is the same or the similar as probe 104 as discussed above with reference to FIG. 1. By replacing or modifying the oxygen saturation probe of a conventional oximeter, the oximeter can be configured to perform spectroscopic measurements of a liquid within a tissue sample as discussed above with reference to FIG. 1A.

After the tissue sample is received, spring mechanism 1204 applies a repeatable force onto housing 1202 and probe (not visible in FIG. 12), which in turn applies a force to the tissue sample.

Figure 13:
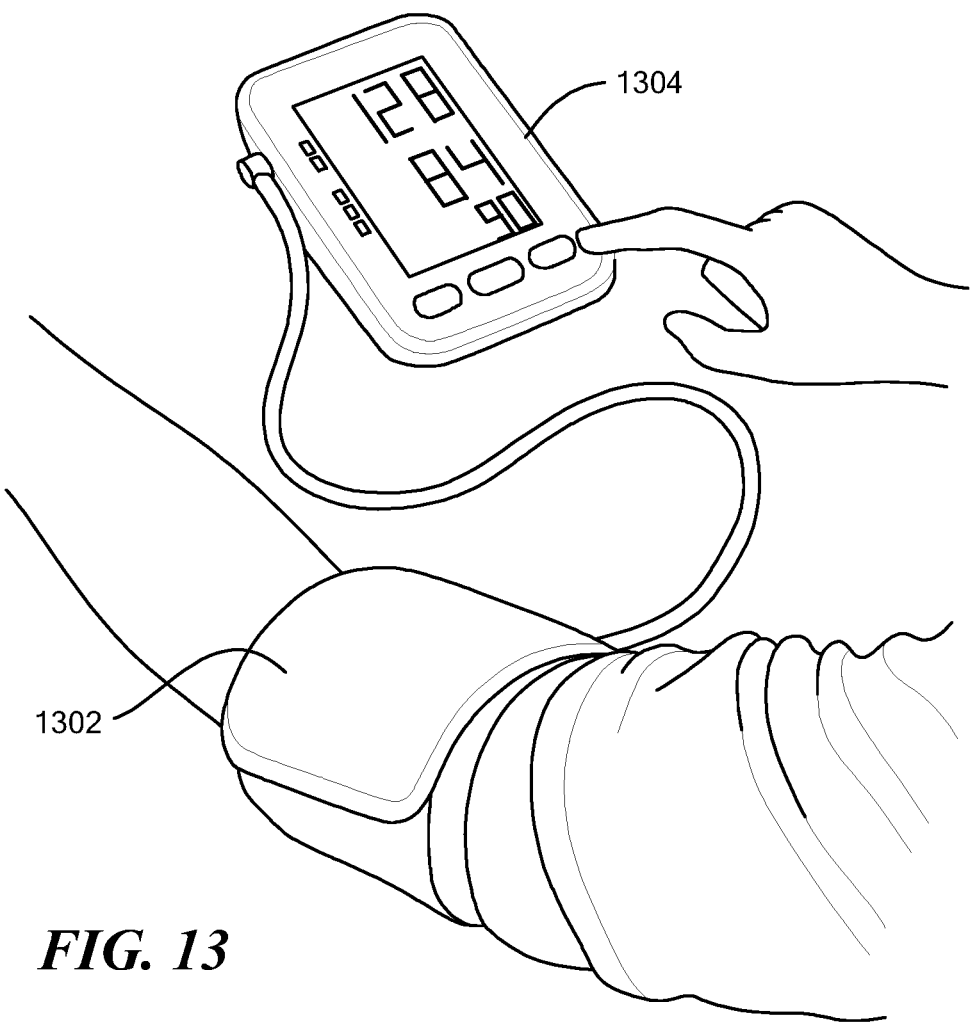
FIG. 13 is an illustration of an example implementation of a noninvasive skin contact sensor, according to an illustrative embodiment.

Referring now to FIG. 13. an example implementation of noninvasive skin contact sensor 100 is provided. In an illustrative implementation, noninvasive skin contact sensor 100 is presented as a modified blood pressure cuff and includes probe 104 (not visible in FIG. 13) and force controller 106 represented here as armband 1302 and pump 1304. Armband 1302 is configured to surround a tissue sample, here represented as a user's arm. Pump 1304 is configured to pump air into armband 1302 causing armband 1302 to inflate and apply a repeatable force onto probe 104 which in turn applies a force to the tissue sample.

Here, a conventional blood pressure cuff may be modified so that probe 104 is disposed on armband 1302 of a conventional blood pressure cuff. Probe 104 can be disposed so that probe 104 comes into contact with at least a portion of a tissue sample when armband 1302 is fastened around the tissue sample. As the fastened armband 1302 inflates due to air being pumped by pump 1304, a repeatable force is applied to probe 104 that is in contact with the tissue sample, so that, in turn, probe 104 applies a repeatable force to the tissue sample.

Figure 14:
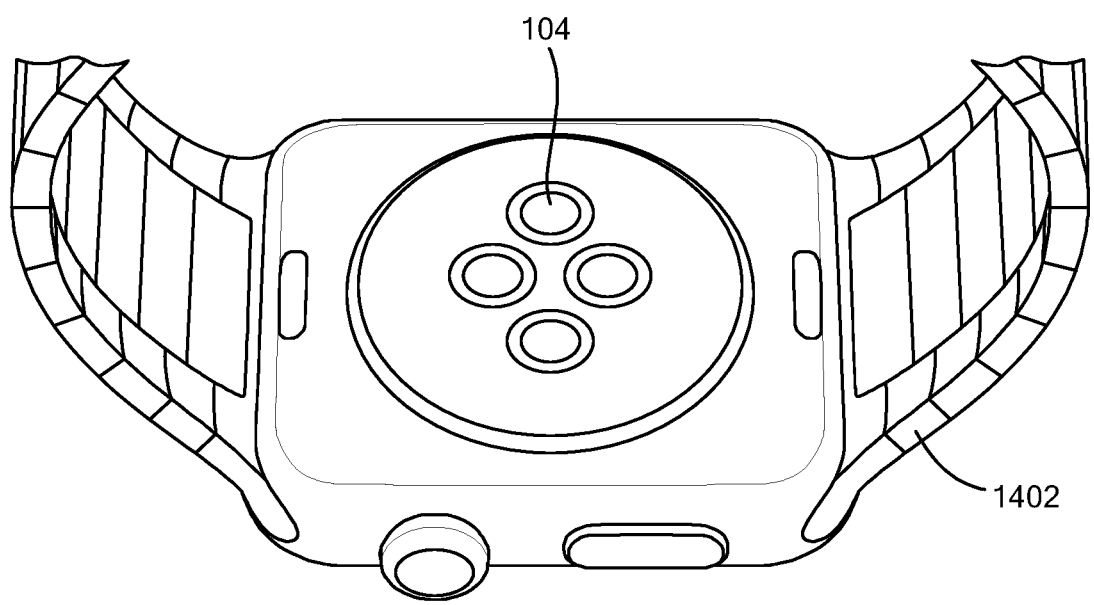
FIG. 14 is an illustration of an example implementation of a noninvasive skin contact sensor, according to an illustrative embodiment.

Referring now to FIG. 14. an example implementation of noninvasive skin contact sensor 100 is provided. In an illustrative implementation, noninvasive skin contact sensor 100 includes probe 104 and force controller 106 represented here as a wristband 1402. Those of ordinary skill in the art will appreciate, of course, that an armband could also be used. Wristband 1402 is configured to strap surround a tissue sample, here represented as a user's wrist. As wristband 1402 straps around the tissue sample, it is configured to apply a repeatable force onto probe 104 as it which in turn applies a force to the tissue sample.

Processing may be implemented in hardware, software, or a combination of the two. Processing may be implemented in computer programs executed on programmable computers/machines that each includes a processor, a storage medium or other article of manufacture that is readable by the processor (including volatile and non-volatile memory and/or storage elements), at least one input device, and one or more output devices. Program code may be applied to data entered using an input device to perform processing and to generate output information.

The system can perform processing, at least in part, via a computer program product, (e.g., in a machine-readable storage device), for execution by, or to control the operation of, data processing apparatus (e.g., a programmable processor, a computer, or multiple computers). Each such program may be implemented in a high-level procedural or object-oriented programming language to communicate with a computer system. However, the programs may be implemented in assembly or machine language. The language may be a compiled or an interpreted language and it may be deployed in any form, including as a stand-alone program or as a module, component, subroutine, or other unit suitable for use in a computing environment. A computer program may be deployed to be executed on one computer or on multiple computers at one site or distributed across multiple sites and interconnected by a communication network. A computer program may be stored on a storage medium or device (e.g., CD-ROM, hard disk, or magnetic diskette) that is readable by a general or special purpose programmable computer for configuring and operating the computer when the storage medium or device is read by the computer. Processing may also be implemented as a machine-readable storage medium, configured with a computer program, where upon execution, instructions in the computer program cause the computer to operate.

Processing may be performed by one or more programmable processors executing one or more computer programs to perform the functions of the system. All or part of the system may be implemented as, special purpose logic circuitry (e.g., an FPGA (field programmable gate array) and/or an ASIC (application-specific integrated circuit)).

Having described illustrative embodiments, it will now become apparent to one of ordinary skill in the art that other embodiments incorporating their concepts may also be used. The embodiments contained herein should not be limited to disclosed embodiments but rather should be limited only by the spirit and scope of the appended claims. All publications and references cited herein are expressly incorporated herein by reference in their entirety.

Elements of different embodiments described herein may be combined to form other embodiments not specifically set forth above. Various elements, which are described in the context of a single embodiment, may also be provided separately or in any suitable sub-combination. Other embodiments not specifically described herein are also within the scope of the following claims.

The invention claimed is:

1. A system for measuring a hydration level in a tissue, the system comprising:
a noninvasive coaxial probe having a first end configured to be in contact with the tissue and configured to emit and receive signals associated with a spectroscopic technique and having a second end adapted to be coupled to transmit and receive circuitry;
a patch coupled to the noninvasive coaxial probe and configured to be adhered to the tissue so as to provide a force that can be repeatedly applied upon at least a portion of the noninvasive coaxial probe configured to be in contact with the tissue wherein the patch applies the force in a manner such that the same force is consistently applied to at least a portion of the tissue over a number of consecutive measurements; and
a signal processing circuitry, coupled to receive signals from the noninvasive coaxial probe, configured to determine an amount of liquid within the portion of the tissue in contact with the first end of the noninvasive coaxial probe.

2. The system of claim 1, wherein the spectroscopic technique comprises one of dielectric, near infrared, or infrared spectroscopy.

3. The system of claim 1, wherein the noninvasive coaxial probe further comprises a temperature probe.

4. The system of claim 1, wherein the signal processing circuitry is further configured to generate an alert when the a determined hydration level is below an underhydration threshold.

5. The system of claim 1, wherein the signal processing circuitry is further configured to track the hydration level for the tissue.

6. The system of claim 1, wherein the signal processing circuitry is further configured to determine determining a change in the hydration level of the tissue.

7. The system of claim 1, wherein the noninvasive coaxial probe is further configured to emit signals associated with dielectric spectroscopy.

8. The system of claim 1, wherein the noninvasive coaxial probe is further configured to emit signals associated with infrared spectroscopy.

* * * * *